US008565880B2

(12) United States Patent
Dong et al.

(10) Patent No.: US 8,565,880 B2
(45) Date of Patent: Oct. 22, 2013

(54) HIS-BUNDLE CAPTURE VERIFICATION AND MONITORING

(75) Inventors: Yanting Dong, Shoreview, MN (US); Allan C. Shuros, St. Paul, MN (US); Jiang Ding, Shoreview, MN (US); Scott A. Meyer, Lakeville, MN (US); Shibaji Shome, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/094,416

(22) Filed: Apr. 26, 2011

(65) Prior Publication Data

US 2011/0264158 A1   Oct. 27, 2011

Related U.S. Application Data

(60) Provisional application No. 61/328,248, filed on Apr. 27, 2010.

(51) Int. Cl.
*A61N 1/36* (2006.01)

(52) U.S. Cl.
USPC .................................................. 607/28; 607/9

(58) Field of Classification Search
USPC ...................................................... 607/4–28
See application file for complete search history.

(56) References Cited

U.S. PATENT DOCUMENTS

| | | |
|---|---|---|
| 3,614,955 A | 10/1971 | Mirowski |
| 3,804,098 A | 4/1974 | Friedman |
| 3,866,615 A | 2/1975 | Hewson |
| 3,911,928 A | 10/1975 | Lagergren |
| 3,942,536 A | 3/1976 | Mirowski et al. |
| 3,949,757 A | 4/1976 | Sabel |
| 3,995,623 A | 12/1976 | Blake et al. |
| 4,026,303 A | 5/1977 | Babotai |
| 4,030,508 A | 6/1977 | Thalen |
| 4,057,067 A | 11/1977 | Lajos |
| 4,106,512 A | 8/1978 | Bisping |
| 4,136,703 A | 1/1979 | Wittkampf |
| 4,154,247 A | 5/1979 | O'Neill |
| 4,217,913 A | 8/1980 | Dutcher |
| 4,258,725 A | 3/1981 | O'Neill |
| 4,278,093 A | 7/1981 | Lafortune et al. |
| 4,282,885 A | 8/1981 | Bisping |

(Continued)

FOREIGN PATENT DOCUMENTS

| | | |
|---|---|---|
| AU | 2005319498 B2 | 7/2011 |
| DE | 2827595 A1 | 4/1979 |

(Continued)

OTHER PUBLICATIONS

"U.S. Appl. No. 10/004,695, Non-Final Office Action mailed Dec. 22, 2003", 6 pgs.

(Continued)

*Primary Examiner* — Joseph Stoklosa
(74) *Attorney, Agent, or Firm* — Schwegman Lundberg & Woessner, P.A.

(57) ABSTRACT

This document discusses, among other things, a system and method for generating a stimulation energy to provide His-bundle stimulation for a cardiac cycle, receiving electrical information from the heart over at least a portion of the cardiac cycle, determining a characteristic of at least a portion of the received electrical information for the cardiac cycle, and classifying the cardiac cycle using the determined characteristic.

18 Claims, 7 Drawing Sheets

(56) References Cited

U.S. PATENT DOCUMENTS

| | | |
|---|---|---|
| 4,289,134 A | 9/1981 | Bernstein |
| 4,289,144 A | 9/1981 | Gilman |
| 4,311,153 A | 1/1982 | Smits |
| 4,332,259 A | 6/1982 | McCorkle, Jr. |
| 4,365,639 A | 12/1982 | Goldreyer |
| 4,393,883 A | 7/1983 | Smyth et al. |
| 4,402,329 A | 9/1983 | Williams |
| 4,437,474 A | 3/1984 | Peers-Trevarton |
| 4,458,677 A | 7/1984 | McCorkle, Jr. |
| 4,458,695 A | 7/1984 | Peers-Trevarton |
| 4,463,765 A | 8/1984 | Gold |
| 4,469,104 A | 9/1984 | Peers-Trevarton |
| 4,497,326 A | 2/1985 | Curry |
| 4,540,236 A | 9/1985 | Peers-Trevarton |
| 4,543,956 A | 10/1985 | Herscovici |
| 4,549,548 A | 10/1985 | Wittkampf et al. |
| 4,559,951 A | 12/1985 | Dahl et al. |
| 4,567,901 A | 2/1986 | Harris |
| 4,570,642 A | 2/1986 | Kane et al. |
| 4,577,643 A | 3/1986 | Beranek |
| 4,589,420 A | 5/1986 | Adams et al. |
| 4,602,645 A | 7/1986 | Barrington et al. |
| 4,603,705 A | 8/1986 | Speicher et al. |
| 4,624,265 A | 11/1986 | Grassi |
| 4,624,266 A | 11/1986 | Kane |
| 4,627,439 A | 12/1986 | Harris |
| 4,630,204 A | 12/1986 | Mortara |
| 4,633,880 A | 1/1987 | Osypka et al. |
| 4,641,649 A | 2/1987 | Walinsky et al. |
| 4,643,201 A | 2/1987 | Stokes |
| 4,646,755 A | 3/1987 | Kane |
| 4,649,937 A | 3/1987 | DeHaan et al. |
| 4,649,938 A | 3/1987 | McArthur |
| 4,664,113 A | 5/1987 | Frisbie et al. |
| 4,667,686 A | 5/1987 | Peers-Travarton |
| H356 H | 11/1987 | Stokes et al. |
| 4,721,115 A | 1/1988 | Owens |
| 4,751,931 A | 6/1988 | Briller et al. |
| 4,784,161 A | 11/1988 | Skalsky et al. |
| 4,785,815 A | 11/1988 | Cohen |
| 4,799,486 A | 1/1989 | DuFault |
| 4,799,493 A | 1/1989 | DuFault |
| 4,819,647 A | 4/1989 | Byers et al. |
| 4,819,661 A | 4/1989 | Heil, Jr. et al. |
| 4,819,662 A | 4/1989 | Heil, Jr. et al. |
| 4,876,109 A | 10/1989 | Mayer et al. |
| 4,886,074 A | 12/1989 | Bisping |
| 4,892,102 A | 1/1990 | Astrinsky |
| 4,895,152 A | 1/1990 | Callaghan et al. |
| 4,922,607 A | 5/1990 | Doan et al. |
| 4,922,927 A | 5/1990 | Fine et al. |
| 4,924,881 A | 5/1990 | Brewer |
| 4,953,564 A | 9/1990 | Berthelsen |
| 4,967,766 A | 11/1990 | Bradshaw |
| 4,972,848 A | 11/1990 | Di Domenico et al. |
| 4,994,078 A | 2/1991 | Jarvik |
| 5,002,067 A | 3/1991 | Berthelsen et al. |
| 5,007,864 A | 4/1991 | Stutz, Jr. |
| 5,016,646 A | 5/1991 | Gotthardt et al. |
| 5,050,601 A | 9/1991 | Kupersmith et al. |
| 5,056,516 A | 10/1991 | Spehr |
| 5,063,932 A | 11/1991 | Dahl et al. |
| 5,076,285 A | 12/1991 | Hess et al. |
| 5,083,564 A | 1/1992 | Scherlag |
| 5,092,879 A | 3/1992 | Jarvik |
| 5,129,404 A | 7/1992 | Spehr et al. |
| 5,144,960 A | 9/1992 | Mehra et al. |
| 5,152,299 A | 10/1992 | Soukup |
| 5,174,289 A | 12/1992 | Cohen |
| 5,179,962 A | 1/1993 | Dutcher et al. |
| 5,181,511 A | 1/1993 | Nickolls et al. |
| 5,223,226 A | 6/1993 | Wittmer et al. |
| 5,242,430 A | 9/1993 | Arenas et al. |
| 5,255,693 A | 10/1993 | Dutcher et al. |
| 5,259,394 A | 11/1993 | Bens |
| 5,259,395 A | 11/1993 | Li |
| 5,267,560 A | 12/1993 | Cohen |
| 5,275,620 A | 1/1994 | Darby et al. |
| 5,282,845 A | 2/1994 | Bush et al. |
| 5,299,569 A | 4/1994 | Wernicke et al. |
| 5,300,108 A | 4/1994 | Rebell et al. |
| 5,304,219 A | 4/1994 | Chernoff et al. |
| 5,306,292 A | 4/1994 | Lindegren |
| 5,313,953 A | 5/1994 | Yomtov et al. |
| 5,320,642 A | 6/1994 | Scherlag |
| 5,324,327 A | 6/1994 | Cohen |
| 5,336,252 A | 8/1994 | Cohen |
| 5,342,414 A | 8/1994 | Mehra |
| 5,344,439 A | 9/1994 | Otten |
| 5,358,516 A | 10/1994 | Myers et al. |
| 5,366,496 A | 11/1994 | Dahl et al. |
| 5,370,665 A | 12/1994 | Hudrlik |
| 5,374,286 A | 12/1994 | Morris |
| 5,381,790 A | 1/1995 | Kanesaka |
| 5,393,929 A | 2/1995 | Yagihashi |
| 5,405,373 A | 4/1995 | Petersson et al. |
| 5,411,544 A | 5/1995 | Mar et al. |
| 5,425,755 A | 6/1995 | Doan |
| 5,433,735 A | 7/1995 | Zanakis et al. |
| 5,439,391 A | 8/1995 | McEtchin et al. |
| 5,447,533 A | 9/1995 | Vachon et al. |
| 5,447,534 A | 9/1995 | Jammet |
| 5,456,706 A | 10/1995 | Pless et al. |
| 5,456,708 A | 10/1995 | Doan et al. |
| 5,466,253 A | 11/1995 | Doan |
| 5,476,497 A | 12/1995 | Mower et al. |
| 5,476,499 A | 12/1995 | Hirschberg |
| 5,476,501 A | 12/1995 | Stewart et al. |
| 5,476,502 A | 12/1995 | Rubin |
| 5,492,119 A | 2/1996 | Abrams |
| 5,500,008 A | 3/1996 | Fain |
| 5,514,172 A | 5/1996 | Mueller |
| 5,515,848 A | 5/1996 | Corbett, III et al. |
| 5,522,874 A | 6/1996 | Gates |
| 5,524,338 A | 6/1996 | Martyniuk et al. |
| 5,527,344 A | 6/1996 | Arzbaecher et al. |
| 5,531,780 A | 7/1996 | Vachon |
| 5,545,201 A | 8/1996 | Helland et al. |
| 5,554,178 A | 9/1996 | Dahl et al. |
| 5,571,163 A | 11/1996 | Helland |
| 5,578,068 A | 11/1996 | Laske et al. |
| 5,593,405 A | 1/1997 | Osypka |
| 5,593,433 A | 1/1997 | Spehr et al. |
| 5,609,158 A | 3/1997 | Chan |
| 5,628,778 A | 5/1997 | Kruse et al. |
| 5,628,779 A | 5/1997 | Bornzin et al. |
| 5,634,829 A | 6/1997 | Kerul |
| 5,634,899 A | 6/1997 | Shapland et al. |
| 5,674,272 A | 10/1997 | Bush et al. |
| 5,674,274 A | 10/1997 | Morgan et al. |
| 5,681,013 A | 10/1997 | Rudolph |
| 5,683,447 A | 11/1997 | Bush et al. |
| 5,702,427 A | 12/1997 | Ecker et al. |
| 5,709,753 A | 1/1998 | Olson et al. |
| 5,716,390 A | 2/1998 | Li |
| 5,718,720 A | 2/1998 | Prutchi et al. |
| 5,720,099 A | 2/1998 | Parker et al. |
| 5,728,140 A | 3/1998 | Salo et al. |
| 5,733,323 A | 3/1998 | Buck et al. |
| 5,755,766 A | 5/1998 | Chastain et al. |
| 5,769,881 A | 6/1998 | Schroeppel et al. |
| 5,772,693 A | 6/1998 | Brownlee |
| 5,782,898 A | 7/1998 | Dahl et al. |
| 5,800,464 A | 9/1998 | Kieval |
| 5,800,465 A | 9/1998 | Thompson et al. |
| 5,807,306 A | 9/1998 | Shapland et al. |
| 5,810,887 A | 9/1998 | Accorti, Jr. et al. |
| 5,814,077 A | 9/1998 | Sholder et al. |
| 5,814,079 A | 9/1998 | Kieval |
| 5,851,227 A | 12/1998 | Spehr |
| 5,871,506 A | 2/1999 | Mower |
| 5,871,529 A | 2/1999 | Bartig et al. |
| 5,871,531 A | 2/1999 | Struble |
| 5,876,399 A | 3/1999 | Chia et al. |

(56) References Cited

U.S. PATENT DOCUMENTS

| | | |
|---|---|---|
| 5,876,431 A | 3/1999 | Spehr et al. |
| 5,916,214 A | 6/1999 | Cosio et al. |
| 5,925,045 A | 7/1999 | Reimels et al. |
| 5,935,159 A | 8/1999 | Cross, Jr. et al. |
| 5,941,868 A | 8/1999 | Kaplan |
| 5,944,710 A | 8/1999 | Dev et al. |
| 5,964,795 A | 10/1999 | McVenes et al. |
| 5,972,416 A | 10/1999 | Reimels et al. |
| 5,995,871 A | 11/1999 | Knisley |
| 6,006,139 A | 12/1999 | Kruse et al. |
| 6,007,476 A | 12/1999 | Wascher et al. |
| 6,024,739 A | 2/2000 | Ponzi et al. |
| 6,059,726 A | 5/2000 | Lee et al. |
| 6,070,104 A | 5/2000 | Hine et al. |
| 6,086,582 A | 7/2000 | Altman et al. |
| 6,096,069 A | 8/2000 | Bischoff |
| 6,123,084 A | 9/2000 | Jandak et al. |
| 6,141,588 A | 10/2000 | Cox et al. |
| 6,141,594 A | 10/2000 | Flynn et al. |
| 6,161,029 A | 12/2000 | Spreigl et al. |
| 6,165,164 A | 12/2000 | Hill et al. |
| 6,212,434 B1 | 4/2001 | Scheiner et al. |
| 6,219,581 B1 | 4/2001 | Schaldach et al. |
| 6,230,061 B1 | 5/2001 | Hartung |
| 6,236,887 B1 | 5/2001 | Ben-Haim et al. |
| 6,254,573 B1 | 7/2001 | Haim et al. |
| 6,256,541 B1 | 7/2001 | Heil et al. |
| 6,267,778 B1 | 7/2001 | Cohen |
| 6,309,370 B1 | 10/2001 | Haim et al. |
| 6,341,235 B1 | 1/2002 | Mower |
| 6,345,204 B1 | 2/2002 | Scheiner et al. |
| 6,358,247 B1 | 3/2002 | Altman et al. |
| 6,363,286 B1 | 3/2002 | Zhu et al. |
| 6,416,510 B1 | 7/2002 | Altman et al. |
| 6,430,441 B1 * | 8/2002 | Levine ............... 607/28 |
| 6,463,334 B1 | 10/2002 | Flynn et al. |
| 6,468,263 B1 | 10/2002 | Fischell et al. |
| 6,471,697 B1 | 10/2002 | Lesh |
| 6,484,057 B2 | 11/2002 | Ideker et al. |
| 6,505,082 B1 | 1/2003 | Peterfeso et al. |
| 6,535,766 B1 | 3/2003 | Thompson et al. |
| 6,540,725 B1 | 4/2003 | Ponzi |
| 6,542,775 B2 | 4/2003 | Ding et al. |
| 6,544,270 B1 | 4/2003 | Zhang |
| 6,547,787 B1 | 4/2003 | Altman et al. |
| 6,556,874 B2 | 4/2003 | Audoglio |
| 6,560,489 B2 | 5/2003 | Hauck |
| 6,575,931 B1 | 6/2003 | Ponzi |
| 6,585,716 B2 | 7/2003 | Altman |
| 6,606,517 B1 | 8/2003 | Park et al. |
| 6,609,027 B2 | 8/2003 | Kroll et al. |
| 6,623,473 B1 | 9/2003 | Ponzi |
| 6,623,474 B1 | 9/2003 | Ponzi |
| 6,643,546 B2 | 11/2003 | Mathis et al. |
| 6,650,940 B1 | 11/2003 | Zhu et al. |
| 6,702,744 B2 | 3/2004 | Mandrusov et al. |
| 6,702,777 B2 | 3/2004 | Haim et al. |
| 6,718,206 B2 | 4/2004 | Casavant |
| 6,766,190 B2 | 7/2004 | Ferek-Petric |
| 6,768,923 B2 | 7/2004 | Ding et al. |
| 6,801,807 B2 | 10/2004 | Abrahamson |
| 6,804,555 B2 | 10/2004 | Warkentin |
| 6,810,286 B2 | 10/2004 | Donovan et al. |
| 6,855,124 B1 | 2/2005 | Gonzalez et al. |
| 6,901,289 B2 | 5/2005 | Dahl et al. |
| 6,905,476 B2 | 6/2005 | Ponzi |
| 6,907,285 B2 | 6/2005 | Denker et al. |
| 6,909,920 B2 | 6/2005 | Lokhoff et al. |
| 6,915,169 B2 | 7/2005 | Flynn et al. |
| 6,931,286 B2 | 8/2005 | Sigg et al. |
| 6,937,897 B2 | 8/2005 | Min et al. |
| 7,027,876 B2 | 4/2006 | Casavant et al. |
| 7,039,462 B2 | 5/2006 | Pastore et al. |
| 7,096,051 B1 | 8/2006 | Alder |
| 7,113,825 B2 | 9/2006 | Pastore et al. |
| 7,130,682 B2 | 10/2006 | Stahmann et al. |
| 7,187,970 B2 | 3/2007 | Shemer et al. |
| 7,245,973 B2 | 7/2007 | Liu et al. |
| 7,257,443 B2 | 8/2007 | Pastore et al. |
| 7,280,872 B1 | 10/2007 | Mosesov et al. |
| 7,317,950 B2 | 1/2008 | Lee |
| 7,319,900 B2 | 1/2008 | Kim et al. |
| 7,359,837 B2 | 4/2008 | Drew |
| 7,392,095 B2 | 6/2008 | Flynn et al. |
| 7,395,042 B2 | 7/2008 | Alder |
| 7,400,931 B2 | 7/2008 | Mandrusov et al. |
| 7,460,914 B2 | 12/2008 | Mandrusov et al. |
| 7,509,170 B2 | 3/2009 | Zhang et al. |
| 7,512,440 B2 | 3/2009 | Ortega et al. |
| 7,529,584 B2 | 5/2009 | Laske et al. |
| 7,792,580 B2 | 9/2010 | Borowitz et al. |
| 7,817,784 B2 | 10/2010 | Wang et al. |
| 8,005,544 B2 | 8/2011 | Zhu et al. |
| 8,010,191 B2 | 8/2011 | Zhu et al. |
| 8,010,192 B2 | 8/2011 | Zhu et al. |
| 8,014,861 B2 | 9/2011 | Zhu et al. |
| 8,050,756 B2 | 11/2011 | Zhu et al. |
| 8,078,287 B2 | 12/2011 | Liu et al. |
| 8,285,376 B2 | 10/2012 | Ortega et al. |
| 8,290,586 B2 | 10/2012 | Zhu et al. |
| 8,326,423 B2 | 12/2012 | Zhu et al. |
| 8,346,358 B2 | 1/2013 | Ortega et al. |
| 8,423,139 B2 | 4/2013 | Zhu et al. |
| 8,428,715 B2 | 4/2013 | Ortega et al. |
| 2001/0031986 A1 | 10/2001 | Hauck |
| 2001/0044619 A1 | 11/2001 | Altman |
| 2002/0010492 A1 | 1/2002 | Donovan et al. |
| 2002/0016615 A1 | 2/2002 | Dev et al. |
| 2002/0022863 A1 | 2/2002 | Hauck |
| 2002/0026228 A1 | 2/2002 | Schauerte |
| 2002/0049478 A1 | 4/2002 | Ding et al. |
| 2002/0058981 A1 | 5/2002 | Zhu et al. |
| 2002/0099413 A1 | 7/2002 | Mower |
| 2002/0120318 A1 | 8/2002 | Kroll et al. |
| 2002/0169484 A1 | 11/2002 | Mathis et al. |
| 2002/0183720 A1 | 12/2002 | Hill et al. |
| 2002/0193836 A1 | 12/2002 | Schmidt |
| 2002/0198583 A1 | 12/2002 | Rock et al. |
| 2003/0009145 A1 | 1/2003 | Struijker-Boudier |
| 2003/0032938 A1 | 2/2003 | Altman |
| 2003/0069625 A1 | 4/2003 | Ley et al. |
| 2003/0078625 A1 | 4/2003 | Casavant |
| 2003/0083711 A1 * | 5/2003 | Yonce et al. ............... 607/27 |
| 2003/0093104 A1 | 5/2003 | Bonner et al. |
| 2003/0105492 A1 | 6/2003 | Ding et al. |
| 2003/0105496 A1 | 6/2003 | Yu et al. |
| 2003/0109914 A1 | 6/2003 | Westlund et al. |
| 2003/0113303 A1 | 6/2003 | Schwartz |
| 2003/0125615 A1 | 7/2003 | Schwartz |
| 2003/0129750 A1 | 7/2003 | Schwartz |
| 2003/0163184 A1 | 8/2003 | Scheiner et al. |
| 2003/0171723 A1 | 9/2003 | Ponzi |
| 2003/0195470 A1 | 10/2003 | Ponzi |
| 2004/0006265 A1 | 1/2004 | Alhussiny |
| 2004/0064176 A1 | 4/2004 | Min et al. |
| 2004/0104782 A1 | 6/2004 | Ruffieux |
| 2004/0106958 A1 | 6/2004 | Mathis et al. |
| 2004/0122484 A1 | 6/2004 | Hatlestad et al. |
| 2004/0153127 A1 | 8/2004 | Gordon et al. |
| 2004/0186546 A1 | 9/2004 | Mandrusov et al. |
| 2004/0213770 A1 | 10/2004 | Seward et al. |
| 2004/0214182 A1 | 10/2004 | Sharma et al. |
| 2004/0215240 A1 | 10/2004 | Lovett et al. |
| 2004/0215249 A1 | 10/2004 | Corbucci |
| 2004/0215251 A1 | 10/2004 | Sharma et al. |
| 2004/0260374 A1 | 12/2004 | Zhang et al. |
| 2005/0049516 A1 | 3/2005 | Ideker |
| 2005/0075677 A1 | 4/2005 | Ganion et al. |
| 2005/0125041 A1 | 6/2005 | Min et al. |
| 2005/0136385 A1 | 6/2005 | Mann |
| 2005/0137671 A1 | 6/2005 | Liu et al. |
| 2005/0152516 A1 | 7/2005 | Wang et al. |
| 2005/0159725 A1 | 7/2005 | Tockman et al. |
| 2005/0203580 A1 | 9/2005 | Prentice et al. |

(56) References Cited

U.S. PATENT DOCUMENTS

| | | |
|---|---|---|
| 2005/0267557 A1 | 12/2005 | Flynn et al. |
| 2005/0277993 A1 | 12/2005 | Mower |
| 2006/0030810 A1 | 2/2006 | Mandrusov et al. |
| 2006/0064027 A1 | 3/2006 | Borowitz et al. |
| 2006/0104596 A1 | 5/2006 | Askins et al. |
| 2006/0116596 A1 | 6/2006 | Zhou et al. |
| 2006/0136001 A1 | 6/2006 | Ortega et al. |
| 2006/0142812 A1 | 6/2006 | Ortega et al. |
| 2006/0224197 A1 | 10/2006 | Havel et al. |
| 2006/0224224 A1 | 10/2006 | Muhlenberg et al. |
| 2007/0027488 A1 | 2/2007 | Kaiser et al. |
| 2007/0060961 A1 | 3/2007 | Echt et al. |
| 2007/0093872 A1 | 4/2007 | Chirife et al. |
| 2007/0093874 A1 | 4/2007 | Chirife et al. |
| 2007/0129764 A1 | 6/2007 | Burnes |
| 2007/0208387 A1 | 9/2007 | Mower |
| 2007/0232949 A1 | 10/2007 | Saksena |
| 2007/0233216 A1 | 10/2007 | Liu et al. |
| 2007/0239219 A1 | 10/2007 | Salo et al. |
| 2008/0262587 A1 | 10/2008 | Flynn et al. |
| 2008/0319496 A1 | 12/2008 | Zhu et al. |
| 2008/0319499 A1 | 12/2008 | Zhu et al. |
| 2008/0319500 A1 | 12/2008 | Zhu et al. |
| 2008/0319501 A1* | 12/2008 | Zhu et al. ............... 607/28 |
| 2009/0005830 A1 | 1/2009 | Zhu et al. |
| 2009/0005832 A1 | 1/2009 | Zhu et al. |
| 2009/0005846 A1 | 1/2009 | Zhu et al. |
| 2009/0054942 A1 | 2/2009 | Zhu et al. |
| 2009/0093859 A1 | 4/2009 | Ortega et al. |
| 2009/0093861 A1 | 4/2009 | Ortega et al. |
| 2009/0099619 A1 | 4/2009 | Lessmeier et al. |
| 2009/0105778 A1 | 4/2009 | Lee et al. |
| 2009/0259272 A1 | 10/2009 | Reddy et al. |
| 2010/0042176 A1 | 2/2010 | Snell |
| 2010/0318147 A1 | 12/2010 | Forslund et al. |
| 2011/0264168 A1 | 10/2011 | Dadd et al. |
| 2011/0307026 A1 | 12/2011 | Zhu et al. |
| 2011/0319772 A1 | 12/2011 | Ingle |
| 2011/0319956 A1 | 12/2011 | Zhu et al. |
| 2012/0041500 A1 | 2/2012 | Zhu et al. |
| 2012/0041503 A1 | 2/2012 | Zhu et al. |
| 2012/0053651 A1 | 3/2012 | Zhu et al. |
| 2012/0101539 A1 | 4/2012 | Zhu et al. |
| 2012/0239106 A1 | 9/2012 | Maskara et al. |
| 2013/0041423 A1 | 2/2013 | Zhu et al. |

FOREIGN PATENT DOCUMENTS

| | | |
|---|---|---|
| DE | 3712082 A1 | 10/1988 |
| EP | 0042551 A1 | 12/1981 |
| EP | 0057877 A1 | 8/1982 |
| EP | 0282047 A2 | 9/1988 |
| EP | 0321764 A1 | 6/1989 |
| EP | 0452278 A2 | 10/1991 |
| EP | 0573275 A2 | 12/1993 |
| EP | 0591053 A1 | 4/1994 |
| EP | 0612538 A2 | 8/1994 |
| EP | 0620024 A1 | 10/1994 |
| EP | 0672431 A2 | 9/1995 |
| EP | 0709111 A2 | 5/1996 |
| EP | 1234597 A2 | 8/2002 |
| FR | 2465489 A1 | 3/1981 |
| FR | 2575925 A1 | 7/1986 |
| FR | 2757773 A1 | 7/1998 |
| GB | 2240721 A | 8/1991 |
| JP | 5501211 A | 3/1993 |
| JP | 10-052507 A | 2/1998 |
| JP | 2008539894 A | 11/2008 |
| WO | WO-92/20401 A1 | 11/1992 |
| WO | WO-94/22525 A1 | 10/1994 |
| WO | WO-96/15665 A2 | 5/1996 |
| WO | WO-97/40883 A1 | 11/1997 |
| WO | WO-00/74773 A1 | 12/2000 |
| WO | WO-03/035170 A1 | 5/2003 |
| WO | WO-2005/011475 A2 | 2/2005 |
| WO | WO-2006/068880 A1 | 6/2006 |
| WO | WO-2008/063498 A1 | 5/2008 |
| WO | WO-2009/006321 A2 | 1/2009 |
| WO | WO-2009/006325 A1 | 1/2009 |
| WO | WO-2009/006327 A1 | 1/2009 |
| WO | WO-2009/006331 A1 | 1/2009 |
| WO | WO-2009/006339 A1 | 1/2009 |
| WO | WO-2009/078751 A1 | 6/2009 |
| WO | WO-2010/042910 A1 | 4/2010 |
| WO | WO-2010/071849 A2 | 6/2010 |
| WO | WO-2011/139691 A1 | 11/2011 |
| WO | WO-2012/005985 A2 | 1/2012 |
| WO | WO-2012125273 A2 | 9/2012 |
| WO | WO-2012125273 A3 | 9/2012 |

OTHER PUBLICATIONS

"U.S. Appl. No. 10/004,695, Notice of Allowance mailed Apr. 13, 2004", 7 pgs.

"U.S. Appl. No. 10/004,695, Response filed Mar. 9, 2004 to Non-Final Office Action mailed Dec. 22, 2003", 8 pgs.

"U.S. Appl. No. 10/745,302, Non-Final Office Action mailed Mar. 14, 2006", 19 pgs.

"U.S. Appl. No. 10/745,302, Non-Final Office Action mailed Sep. 14, 2006", 14 pgs.

"U.S. Appl. No. 10/745,302, Non-Final Office Action mailed Sep. 23, 2005", 11 pgs.

"U.S. Appl. No. 10/745,302, Notice of Allowance mailed Mar. 12, 2007", 4 pgs.

"U.S. Appl. No. 10/745,302, Response filed Jun. 26, 2006 to Non Final Office Action mailed Mar. 14, 2006", 16 pgs.

"U.S. Appl. No. 10/745,302, Response filed Sep. 12, 2005 to Restriction Requirement mailed Aug. 12, 2005", 6 pgs.

"U.S. Appl. No. 10/745,302, Response filed Dec. 14, 2006 to Non Final Office Action mailed Sep. 14, 2006", 13 pgs.

"U.S. Appl. No. 10/745,302, Response filed Dec. 23, 2005 to Non Final Office Action mailed Sep. 23, 2005", 15 pgs.

"U.S. Appl. No. 10/745,302, Restriction Requirement mailed Aug. 12, 2005", 7 pgs.

"U.S. Appl. No. 11/300,242, Final Office Action mailed Aug. 4, 2009", 9 pgs.

"U.S. Appl. No. 11/300,242, Non Final Office Action mailed May 12, 2011", 9 pgs.

"U.S. Appl. No. 11/300,242, Non-Final Office Action mailed Mar. 27, 2008", 8 pgs.

"U.S. Appl. No. 11/300,242, Notice of Allowance mailed Jan. 24, 2012", 5 pgs.

"U.S. Appl. No. 11/300,242, Notice of Allowance mailed Mar. 8, 2012", 6 pgs.

"U.S. Appl. No. 11/300,242, Notice of Allowance mailed Aug. 24, 2012", 7 pgs.

"U.S. Appl. No. 11/300,242, Response filed Feb. 4, 2010 to Final Office Action mailed Aug. 4, 2009", 11 pgs.

"U.S. Appl. No. 11/300,242, Response filed Apr. 2, 2009 to Restriction Raquirement mailed Dec. 15, 2008", 8 pgs.

"U.S. Appl. No. 11/300,242, Response filed Sep. 12, 2011 to Non Final Office Action mailed May 12, 2011", 8 pgs.

"U.S. Appl. No. 11/300,242, Response filed Sep. 26, 2008 to Non-Final Office Action mailed Mar. 27, 2008", 10 pgs.

"U.S. Appl. No. 11/300,242, Restriction Requirement mailed Dec. 15, 2008", 10 pgs.

"U.S. Appl. No. 11/300,611, 312 Amendment filed Feb. 9, 2009", 9 pgs.

"U.S. Appl. No. 11/300,611, Non-Final Office Action mailed Mar. 20, 2008", 7 pgs.

"U.S. Appl. No. 11/300,611, Notice of Allowance mailed Jan. 26, 2009", 7 pgs.

"U.S. Appl. No. 11/300,611, PTO Response to 312 Amendment mailed Feb. 26, 2009", 3 pgs.

"U.S. Appl. No. 11/300,611, Response filed Sep. 22, 2008 to Non-Final Office Action mailed Mar. 20, 2008", 12 pgs.

"U.S. Appl. No. 12/147,292, Notice of Allowance mailed Apr. 8, 2011", 12 pgs.

(56) References Cited

OTHER PUBLICATIONS

"U.S. Appl. No. 12/147,293, Response filed Feb. 8, 2011 to Restriction Requirement mailed Oct. 8, 2010", 9 pgs.
"U.S. Appl. No. 12/147,293, Restriction Requirement mailed Oct. 8, 2010", 12 pgs.
"U.S. Appl. No. 12/147,317, Response filed Apr. 11, 2012 to Final Office Action mailed Oct. 12, 2011", 8 pgs.
"U.S. Appl. No. 12/147,317, Examiner Interview Summary mailed Mar. 15, 2011", 3 pgs.
"U.S. Appl. No. 12/147,317, Final Office Action mailed Oct. 12, 2011", 6 pgs.
"U.S. Appl. No. 12/147,317, Non-Final Office Action mailed Dec. 28, 2010", 7 pgs.
"U.S. Appl. No. 12/147,317, Notice of Allowance mailed Jul. 2, 2012", 7 pgs.
"U.S. Appl. No. 12/147,317, Response filed Jun. 27, 2011 to Non Final Office Action mailed Dec. 28, 2010", 11 pgs.
"U.S. Appl. No. 12/147,339, Notice of Allowance mailed Mar. 30, 2011", 9 pgs.
"U.S. Appl. No. 12/147,339, Notice of Allowance mailed Dec. 22, 2010", 8 pgs.
"U.S. Appl. No. 12/147,339, Response filed Oct. 20, 2010 to Restriction Requirement mailed Oct. 8, 2010", 7 pgs.
"U.S. Appl. No. 12/147,339, Restriction Requirement mailed Oct. 8, 2010", 7 pgs.
"U.S. Appl. No. 12/147,356, Notice of Allowance mailed Feb. 10, 2011", 17 pgs.
"U.S. Appl. No. 12/147,356, Notice of Allowance mailed Jun. 30, 2011", 15 pgs.
"U.S. Appl. No. 12/147,356, Response filed Nov. 10, 2010 to Restriction Requirement mailed Oct. 12, 2010", 9 pgs.
"U.S. Appl. No. 12/147,356, Restriction Requirement mailed Oct. 12, 2010", 7 pgs.
"U.S. Appl. No. 12/147,369, Non-Final Office Action mailed Sep. 10, 2010", 10 pgs.
"U.S. Appl. No. 12/147,369, Notice of Allowance mailed Apr. 21, 2011", 7 pgs.
"U.S. Appl. No. 12/147,369, Response filed Feb. 10, 2011 to Non Final Office Action mailed Sep. 10, 2010", 7 pgs.
"U.S. Appl. No. 12/147,376, Response filed Feb. 29, 2012 to Non Final Office Action mailed Oct. 3, 2011", 6 pgs.
"U.S. Appl. No. 12/147,376, Final Office Action mailed Apr. 20, 2011", 11 pgs.
"U.S. Appl. No. 12/147,376, Non Final Office Action mailed Oct. 3, 2011", 8 pgs.
"U.S. Appl. No. 12/147,376, Non-Final Office Action mailed Sep. 15, 2010", 9 pgs.
"U.S. Appl. No. 12/147,376, Notice of Allowance mailed Mar. 19, 2012", 7 pgs.
"U.S. Appl. No. 12/147,376, Notice of Allowance mailed Aug. 30, 2012", 7 pgs.
"U.S. Appl. No. 12/147,376, Response filed Feb. 15, 2011 to Non Final Office Action mailed Sep. 15, 2010", 9 pgs.
"U.S. Appl. No. 12/147,376, Response filed Aug. 22, 2011 to Final Office Action mailed Apr. 20, 2011", 8 pgs.
"U.S. Appl. No. 12/147,425, Non-Final Office Action mailed Sep. 15, 2010", 10 pgs.
"U.S. Appl. No. 12/147,425, Notice of Allowance mailed Apr. 19, 2011", 8 pgs.
"U.S. Appl. No. 12/147,425, Response filed Feb. 15, 2011 to Non Final Office Action mailed Sep. 15, 2010", 8 pgs.
"U.S. Appl. No. 12/249,454, Examiner Interview Summary mailed Feb. 22, 2012", 3 pgs.
"U.S. Appl. No. 12/249,454, Final Office Action mailed Nov. 23, 2011", 8 pgs.
"U.S. Appl. No. 12/249,454, Non Final Office Action mailed Apr. 6, 2011", 8 pgs.
"U.S. Appl. No. 12/249,454, Non Final Office Action mailed Sep. 4, 2012", 8 pgs.
"U.S. Appl. No. 12/249,454, Response filed Apr. 2, 2012 to Final Office Action mailed Nov. 23, 2011", 12 pgs.
"U.S. Appl. No. 12/249,454, Response filed Aug. 30, 2011 to Non Final Office Action mailed Apr. 6, 2011", 14 pgs.
"U.S. Appl. No. 12/249,479, Final Office Action mailed Dec. 2, 2011", 8 pgs.
"U.S. Appl. No. 12/249,479, Non Final Office Action mailed Apr. 5, 2011", 10 pgs.
"U.S. Appl. No. 12/249,479, Non Final Office Action mailed Sep. 4, 2012", 7 pgs.
"U.S. Appl. No. 12/249,479, Response filed Apr. 2, 2012 to Final Office Action mailed Dec. 2, 2011", 9 pgs.
"U.S. Appl. No. 12/249,479, Response filed Aug. 30, 2011 to Non Final Office Action mailed Apr. 5, 2011", 12 pgs.
"U.S. Appl. No. 12/249,508, Notice of Allowance mailed Feb. 14, 2012", 7 pgs.
"U.S. Appl. No. 12/249,508, Notice of Allowance mailed Jun. 12, 2012", 7 pgs.
"U.S. Appl. No. 12/249,508, Notice of Allowance mailed Oct. 5, 2011", 9 pgs.
"U.S. Appl. No. 12/249,508, Response filed Aug. 30, 2011 to Restriction Requirement mailed Jun. 30, 2011", 8 pgs.
"U.S. Appl. No. 12/249,508, Restriction Requirement mailed Jun. 30, 2011", 6 pgs.
"U.S. Appl. No. 12/412,608, Final Office Action mailed Nov. 21, 2011", 6 pgs.
"U.S. Appl. No. 12/412,608, Non Final Office Action mailed May 26, 2011", 8 pgs.
"U.S. Appl. No. 12/412,608, Notice of Allowance mailed Jun. 6, 2012", 7 pgs.
"U.S. Appl. No. 12/412,608, Response filed Apr. 18, 2012 to Final Office Action mailed Nov. 21, 2011", 7 pgs.
"U.S. Appl. No. 12/412,608, Response filed Sep. 26, 2011 to Non Final Office Action mailed May 26, 2011", 9 pgs.
"ATROSTIM Phrenic Nerve Stimulator", Product Brochure, AtroTech Oy, P.O. Box 28, FIN-33721 Tampere, Finland, (Jun. 2004), 2 pgs.
"Australian Application Serial No. 2005319498, First Examiner Report mailed May 27, 2010", 3 pgs.
"Australian Application Serial No. 2005319498, Response filed Feb. 21, 2011 to First Examiner Report mailed May 27, 2010", 11 pgs.
"Coating Process for Composite Implants", Medical Materials Update, vol. 1, No. 12, (Jan. 1995), 3 pgs.
"European Application Serial No. 05849548.2, Communication and Supplementary Partial European Search Report mailed Feb. 29, 2008", 8 pgs.
"European Application Serial No. 05849548.2, Communication mailed Jun. 9, 2009", 3 pgs.
"European Application Serial No. 05849548.2, Office Action mailed Dec. 20, 2010", 4 pgs.
"European Application Serial No. 05849548.2, Response filed Jun. 29, 2011 to Non Final Office Action mailed Dec. 20, 2010", 9 pgs.
"European Application Serial No. 05849548.2, Response filed Dec. 16, 2009 to Communication mailed Jun. 9, 2009", 10 pgs.
"European Application Serial No. 08772198.1, Office Action mailed Sep. 13, 2010", 6 pgs.
"European Application Serial No. 08772198.1, Response filed Mar. 31, 2011 to Communication mailed Sep. 30, 2010", 11 pgs.
"European Application Serial No. 08781107.1, Invitation Pursuant to Rule 63(1) EPC mailed Jul. 13, 2010", 3 pgs.
"European Application Serial No. 08781107.1, Communication dated Feb. 9, 2010", 2 pgs.
"European Application Serial No. 08781107.1, Extended European Search Report mailed Nov. 25, 2010", 6 pgs.
"European Application Serial No. 08781107.1, Response filed Mar. 5, 2010 to Communication dated Feb. 9, 2010", 2 pgs.
"European Application Serial No. 08781107.1, Response filed Jun. 14, 2011 to Communication mailed Dec. 14, 2010", 10 pgs.
"European Application Serial No. 08781107.1, Response filed Sep. 22, 2010 to the Invitation to Rule 63(1)", 11 pgs.
"European Application Serial No. 08796045.6, European Search Report mailed Sep. 21, 2010", 6 pgs.

(56) References Cited

OTHER PUBLICATIONS

"European Application Serial No. 08796045.6, Office Action mailed Jan. 4, 2012", 4 pgs.
"European Application Serial No. 08796045.6, Response filed Apr. 15, 2011 to Communication dated Oct. 8, 2010", 10 pgs.
"European Application Serial No. 08796045.6, Response filed May 14, 2012 to Office Action mailed Jan. 4, 2012", 8 pgs.
"Implant Attaches to Bone by Chemical Bond", Medical Materials Update, vol. 4, No. 7, (Aug. 1997), 2 pgs.
"International Application Serial No. PCT/US05/45044, International Search Report mailed May 2, 2006", 1 pg.
"International Application Serial No. PCT/US05/45044, Written Opinion mailed May 2, 2006", 3 pgs.
"International Application Serial No. PCT/US08/68618, International Search Report mailed Nov. 26, 2008", 2 pgs.
"International Application Serial No. PCT/US08/68618, Written Opinion mailed Nov. 26, 2008", 6 pgs.
"International Application Serial No. PCT/US08/68627, International Search Report mailed Sep. 10, 2008", 1 pg.
"International Application Serial No. PCT/US08/68627, Written Opinion maiied Sep. 10, 2008", 4 pgs.
"International Application Serial No. PCT/US08/68630, International Search Report mailed Sep. 10, 2008", 1 pg.
"International Application Serial No. PCT/US08/68630, Written Opinion mailed Sep. 10, 2008", 4 pgs.
"International Application Serial No. PCT/US08/68632, International Search Report mailed Sep. 11, 2008", 2 pgs.
"International Application Serial No. PCT/US08/68632, Written Opinion mailed Sep. 11, 2008", 4 pgs.
"International Application Serial No. PCT/US08/68647, International Search Report mailed Sep. 22, 2008", 2 pgs.
"International Application Serial No. PCT/US08/68647, Written Opinion mailed Sep. 22, 2008", 4 pgs.
"International Application Serial No. PCT/US08/68654, International Search Report mailed Sep. 22, 2008", 2 pgs.
"International Application Serial No. PCT/US08/68654, Written Opinion mailed Sep. 22, 2008", 4 pgs.
"International Application Serial No. PCT/US2008/068635, International Search Report mailed Sep. 9, 2008", 3 pgs.
"International Application Serial No. PCT/US2008/068635, Written Opinion mailed Sep. 9, 2008", 4 pgs.
"International Application Serial No. PCT/US2009/060293, International Preliminary Report on Patentability mailed Apr. 12, 2011", 10 pgs.
"International Application Serial No. PCT/US2009/060293, International Search Report mailed Mar. 10, 2010", 6 pgs.
"International Application Serial No. PCT/US2009/060293, Invitation to Pay Additional Fee mailed Dec. 18, 2009", 5 pgs.
"International Application Serial No. PCT/US2009/060293, Written Opinion mailed Mar. 10, 2010", 10 pgs.
"International Application Serial No. PCT/US2009/068859, International Search Report mailed Jul. 5, 2010", 7 pgs.
"International Application Serial No. PCT/US2009/068859, Invitation to Pay Additional Fee mailed Apr. 15, 2010", 6 pgs.
"International Application Serial No. PCT/US2009/068859, Written Opinion mailed Jul. 5, 2010", 12 pgs.
"International Application Serial No. PCT/US2011/033944, International Search Report mailed Sep. 8, 2011", 5 pgs.
"International Application Serial No. PCT/US2011/033944, Written Opinion mailed Sep. 8, 2011", 9 pgs.
"Japanese Application Serial No. 2007-548289, Final Office Action dated Aug. 2, 2011", (w/ English Translation), 5 pgs.
"Japanese Application Serial No. 2007-548289, Office Action mailed Mar. 6, 2012", (w/ English Translation), 3 pgs.
"Japanese Application Serial No. 2007-548289, Office Action mailed Nov. 24, 2010", (w/ English Translation), 7 pgs.
"Japanese Application Serial No. 2007-548289, Response filed May 20, 2011 to Office Action mailed Nov. 24, 2010", (w/ English Translation of Amended Claims), 9 pgs.

"Japanese Application Serial No. 2007-548289, Response filed Jun. 4, 2012 to Office Action mailed Mar. 6, 2012", 3 pgs.
"Japanese Application Serial No. 2007-548289, Response filed Oct. 26, 2011 to Office Action mailed Aug. 3, 2011", (w/ English Translation of Amended Claims), 10 pgs.
"Victrex's PEEK Used for Dialysis Machines", Medical Material's Update, vol. 3, No. 3, (Apr. 1996), pp. 1-2.
Alboni, P., "Bundle Branch Blocks Anatomically Located in the His Bundle", Italian Cardiology Journal, 10(12), (w/ English Translation thereof, followed by Italian publication), (1980), 1583-1587.
Al-Khadra, A., et al., "The Role of Electroporation in Defibrillation", Circulation Research, 87(9), (Oct. 2000), 797-804.
Arcot-Krishnamurthy, S., et al., "Timing for His-Bundle Pacing", U.S. Appl. No. 13/277,617, filed Oct. 20, 2011, 40 pgs.
Avitall, B., et al., "Iontophoretic Transmyocardial Drug Delivery. A Novel Approach to Antiarrhythmic Drug Therapy", Circulation, 85(4), (1992), 1582-1593.
Barba-Pichardo, Rafael, et al., "Permanent His-Bundle Pacing in Patients With Infra-Hisian Atrioventricular Block", Rev Esp Cardiol. 59(6), (Mar. 9, 2006), 553-558.
Barton, A. J., et al., "Bacterial Adhesion to Orthopedic Implant Polymers", J. Biomed. Mat. Res., 30(3), (Mar. 1996), 403-410.
Bonanno, C., et al., "Effect on QRS Duration and Feasibility of Septal and Multisite Right Ventricular Pacing", Cardiostimolazione, 14(3), (Abstract Only), (Sep. 1996), p. 195.
Buckingham, Thomas A., et al., "Acute Hemodynamic Effects of Atrioventricular Pacing at Differing Sites in the Right Ventricle Individually and Simultaneously", PACE, 20[Pt. I], (Apr. 1997), 909-915.
Cantu, F., et al., "Validation of Criteria for Selective His Bundle and Para-Hisian Permanent Pacing", PACE, vol. 29, (Dec. 2006), 1326-1333.
Cantu, Francesco, et al., "A Methodical Approach to Validate Selective His Bundle and para-Hisian Permanent Pacing", [abstract] Oasis, (2006), 1 pg.
Catanzariti, Domenico, et al., "Permanent His Bundle Pacing Does Not Induce Ventricular Dyssynchrony. An Echocardiographic Intrapatient Study of Comparison with Conventional Pacing", [abstract] Oasis, (2006), 1 pg.
Chiu, L., et al., "Method for One-Click Deployment and or Configuration of Real-Time Software System Modifications", U.S. Appl. No. 60/558,921, filed Apr. 2, 2004, 8 pgs.
Chudzik, Michal, "Ventricular Endocardial Right Bifocal Stimulation in Treatment of Severe Dilated Cardiomyopathy Heart Failure in Patients with Unsuccessful Biventricular Pacemaker Impiantation", [abstract CP07] Europace Supplements, vol. 7, (May 2005), 1 pg.
Deshmukh, P., et al., "Permanent, Direct His-Bundle Pacing: A Novel Approach to Cardiac Pacing in Patients With Normal His-Purkinje Activation", Circulation, 101(8), (Feb. 29, 2000), 869-877.
Deshmukh, Pramod M., et al., "Direct His-Bundle Pacing: Present and Future", PACE, vol. 27, Part II, (Jun. 2004), 862-870.
Dong, Y., et al., "His-Bundle Capture Verification and Monitoring", U.S. Appl. No. 61/328,248, filed Apr. 27, 2010, 40 pgs.
El-Sherif, N., et al., "Normalization of Bundle Branch Block Patterns by Distal His Bundle Pacing: Clinical and Experimental Evidence of Longitudinal Dissociation in the Pathologic His Bundle", Circulation, 57(3), (Mar. 1978), 473-483.
Flynn, David M, et al., "Extendable and Retractable Lead Having a Snap-Fit Terminal Connector", U.S. Appl. No. 11/173,664, filed Jul. 1, 2005, 53 pgs.
Furman, S., et al., "Chapter 5—Permanent Pacemaker Implementation", A Practice of Cardiac Pacing, Futura Publishing Co., Inc. Mount Kisco, NY, (1986), 97-127.
Genc, S., et al., "Methodology for Locking Feature Selection in Integral Snap-Fit Assembly", Proceedings of DETC '97, 1997 ASME Engineering Technical Conferences, (Sep. 1997), 1-11.
Golia, P., et al., "Multisite Pacing of Right Ventricle in Heart Failure: Echocardiographic Evaluation", [Abstract] Cardiostimolazione, vol. 14, No. 3, (Sep. 1996), 5 pgs.
Grosfeld, M. J.W., et al., "Testing a New Mechanism for Left Interventricular Septal Pacing: The Transseptal Route", Europace, vol. 4, (Oct. 2002), 439-444.

(56) References Cited

OTHER PUBLICATIONS

Ha, S. W., et al., "Plasma-Sprayed Hydroxylapatite Coating on Carbon Fibre Reinforced Thermoplastic Composite Materials", J. Mater. Sci. Mater. Med., vol. 5, No. 6-7, (1994), pp. 481-484.
Hummel, J. D., et al., "Augmentation of Cardiac Output by Anodal Pacing", [Abstract] Circulation, 90(No. 4, Part 2), (Oct. 1994), p. I-69.
Ingle, Frank, et al., "Lead Motion Sensing Via Cable Microphonics", U.S. Appl. No. 61/359,430, filed Jun. 29, 2010, 52 pgs.
Jockisch, K. A., et al., "Biological Response to Chopped-Carbon-Fiber-Reinforced Peek", J. Biomed. Mater. Res., vol. 26, No. 2, (1992), pp. 133-146.
Kanno, S., et al., "Establishment of a simple and practical procedure applicable to therapeutic angiogenesis", Circulation, 99(20), (May 25, 1999), 2682-2687.
Kavanagh, K. M., et al., "Monophasic Versus Biphasic Cardiac Stimulation: Mechanism of Decreased Energy Requirements", PACE, vol. 13, No. 10, (Oct. 1990), 10 pgs.
Kaye, D. M., et al., "Frequency-dependent activation of a constitutive nitric oxide synthase and regulation of contractile function in adult rat ventricular myocytes", Circulation Research, 78(2), (Feb. 1996), 217-24.
Knapp, C. P. et al., "Snap Fit Terminal Connector", U.S. Appl. No. 09/184,226, filed Nov. 2, 1998, 39 pgs.
Kutarski, A., et al., "Factors Influencing Differences of RVA & RVOT Pacing Hemodynamic Effects", [abstract CP05] Europace Supplements, vol. 7, (May 2005), p. 288.
Kutarski, A., et al., "Right Ventricular Outflow Tract and Dual Site Right Ventricular Pacing—The Comparison With Apex Pacing", [abstract CP08] Europace Supplements, vol. 7, (May 2005), p. 288.
Labhasetwar, V., et al., "Iontophoresis for Modulation of Cardiac Drug Delivery in Dogs", Proc. Natl. Acad.Sci. USA, 92(7), (Mar. 28, 1995), 2612-2616.
Lazarus, A., et al., "Reduction in Energy Pacing Thresholds by Overlapping Biphasic Stimulation Versus Conventional Bipolar Pacing", PACE, vol. 21, (Nov. 1998), 6 pgs.
Lin, T. W., et al., "Glass Peek Composite Promotes Proliferation and Osteocalcin of Human Osteoblastic Cells", J. Biomed. Mater. Res., vol. 36, No. 2, (1997), pp. 137-144.
Lupi, G., et al., "Effects of Right Ventricular Pacing on Intra-Left Ventricular Electromechanical Activation in Patients with Native Narrow QRS.", American Journal of Cardiology, vol. 98, (2006), 219-222.
MacNair, R., et al., "The Response of Primary Rat and Human Osteoblasts and an Immortalized Rat Osteoblast Cell Line to Orthopaedic Materials: Comparative Sensitivity of Several Toxicity Indices", J. Mater. Sci. Mater. Med., vol. 8, No. 2, (1997), pp. 105-111.
Manolis, Antonis S., "The Deleterious Consequences of Right Ventricular Apical Pacing: Time to Seek Alternate Site Pacing", PACE, vol. 29, (Mar. 2006), 298-315.
Mansourati, J., et al., "Left ventricular-based pacing in patients with chronic heart failure: comparison of acute hemodynamic benefits according to underlying heart disease", Eur J Heart Fail., 2 2), (Jun. 2000), 195-9.
Meyer, M. R., et al., "Long-Term Durability of the Interface in FRP Composites After Exposure to Simulated Physiologic Saline Environments", J. Biomed. Mater. Res., 28(10), (1994), 1221-1231.
Mond, Harry G., et al., "The Right Ventricular Outflow Tract: The Road to Septal Pacing", PACE, vol. 30, (Apr. 2007), 482-491.
Morina-Vazquez, Pablo, et al., "Cardiac Resynchronization Through Selective His Bundle Pacing in a Patient with the So-Called InfraHis Atrioventricular Block", PACE, vol. 28, (Jul. 2005), 726-729.
Morrison, C., et al., "In Vitro Biocompatibility Testing of Polymers for Orthopaedic Implants Using Cultured Fibroblasts and Osteoblasts", Biomaterials, vol. 16, No. 13, (1995), pp. 987-992.
Narula, O. S., "Longitudinal Dissociation in the His Bundle. Bundle Branch Block Due to Asynchronous Conduction Within the His Bundle in Man", Circulation, 56(6), (Dec. 1977), 996-1006.

Occhetta, E., et al., "Prevention of Ventricular Desynchronization by Permanent Para-Hisian Pacing After Atrioventricular Node Ablation in Chronic Atrial Fibrillation: A Crossover, Blinded, Randomized Study Versus Apical Right Ventricular Pacing", Journal of the American College of Cardiology, 47(10), (May 16, 2006), 1938-1945.
Padeletti, Luigi, et al., "Physiologic Pacing: New Modalities and Pacing Sites", PACE, vol. 29, Supplement 2, (Dec. 2006), S73-S77.
Pastore, G., et al., "Different Degree of Ventricular Dyssyncrony Induced by Right Apical, Hissian and Para Hissian Ventricular Pacing", [abstract] Oasis, (2006), 1 pg.
Pastore, Gianni, et al., "Direct His-Bundle Pacing Preserves the Normal Left Activation Sequence: An Acute Echocardiographic Study", [abstract] Oasis, (2006), 1 pg.
Puech, P., et al., "Narrowing and normalization of QRS stimulation of the His bundle in complete left bundle branch block.", Scholarly Journal of the French Cardiology Society, vol. 72, No. 8, (w/ English Translation thereof, followed by French publication), (Aug. 1979), 815-824.
Qu, J, et al., "HCN2 overexpression in newborn and adult ventricular myocytes: distinct effects on gating and excitability", Circ. Res., vol. 89(1), (Jul. 6, 2001), e8-14.
Qu, J, et al., "Sympathetic innervation alters activations of pacemaker current (If) in rat ventricle", J. Physiol, 526 Pt 3, (Aug. 1, 2000), 561-569.
Ravazzi, A., et al., "Improvement of Interventricular Activation Time Using Biphasic Pacing Pulses at Different Sites on Right Ventricle Septal Wall", Progress in Biomedical Research, 4(3), (Jun. 1999), 248-253.
Reddy, G. S., "Bundle of His Stimulation System", U.S. Appl. No. 61/045,168, filed Apr. 15, 2008, 37 pgs.
Saksena, S., et al., "Chapter 9—Pacemaker Implantation Techniques", Electrical Therapy for Cardiac Arrhythmias, W.B. Saunders Co., Philadelphia, PA, (1990), pp. 173, 181-183.
Scheinman, M. M., et al., "Long-Term His-Bundie Pacing and Cardiac Function", Circulation, 101(8), (2000), 836-837.
Schoenfeld, M. H., "Alternative Site Pacing to Promote Cardiac Synchrony: Has Conventional Pacing Become Unconventional?", Journal of the American College of Cardiology, 47(10), (2006), 1946-1948.
Shi, W, et al., "Distribution and prevalence of hyperpolarization-activated cation channel (HCN) mRNA expression in cardiac tissues", Circ. Res., vol. 85(1), (Jul. 9, 1999), e1-6.
Sotobata, I., et al., "Population distribution of Frank-vectorcardiographic measurements of healthy Japanese men", Japanese Circulation Journal, 39(8), (1975), 895-903.
Soyer, J., et al., "Experimental Characterisation of a Carbon/PEEK Hip Prothesis in Fatigue", Chirurgie, 121, (1996), p. 658-663.
Sweeney, M. O., et al., "Adverse Effect of Ventricular Pacing on Heart Failure and Atrial Fibrillation Among Patients with Normal Baseline QRS Duration in a Clinical Trial of Pacemaker Therapy for Sinus Node Dysfunction", Circulation, 107(23), (2003), 2932-2937.
Sweeney, M. O., et al., "Heart Failure During Cardiac Pacing", Circulation, 113(17), (2006), 2082-2088.
Takatsuki, et al., "Clinical Implications of "pure" Hisian pacing in addition to para-Hisian pacing for the diagnosis of supraventricular tachycardia", Heart Rhythm 3 (12), (Dec. 8, 2006), 1412-1418.
Tanabe, M., et al., "Biventricular Pacing Worsened Dyssynchrony in Heart Failure Patient with Right-Bundle Branch Block", International Journal of Cardiology, 138(3), (available online Aug. 15, 2008 / epub doi:10.1016/j.ijcard.2008.06.063 ), (2010), e47-e50.
Thakral, A, et al., "Effects of anodal vs. cathodal pacing on the mechanical performance of the isolated rabbit heart", J. Appl Physiol., 89(3), (Sep. 2000), 1159-64.
Tse, Hung-Fat, et al., "Selection of Permanent Ventricular Pacing Site: How Far Should We Go?", Journal of the American College of Cardiology, 48(8), (Sep. 26, 2006), 1649-1651.
Van Gelder, B. M., et al., "Hemodynamic Effect of RV Apex vs RV Septum Pacing in a Monoventricular and Biventricuiar Configuration in Patients with Heart Failure", [abstract CP06] Europace Supplements, vol. 7, (May 2005), p. 288.

(56) References Cited

OTHER PUBLICATIONS

Victor, F., et al., "A Randomized Comparison of Permanent Septal Versus Apical Right Ventricular Pacing: Short-Term Results", Journal of Cardiovascular Electrophysiology, 17(3), (Mar. 2006), 238-242.
Wang, S. C.-J., et al., "Improved Method and System for Managing Voice Prompt Recordings Prior to Deployment", U.S. Appl. No. 60/532,271, filed Dec. 23, 2003, 12 pgs.
Wenz, L. M., et al., "In Vitro Biocompatibility of Polyetheretherketone and Polysulfone Composites", J. Biomed. Mater. Res., vol. 26, No. 2, (1990), pp. 207-215.
Winckels, S. K. G., et al., "High-Septal Pacing Reduces Ventricular Electrical Remodeling and Proarrhythmia in Chronic Atrioventricular Block Dogs", Journal of the American College of Cardiology, 50(9), (Aug. 28, 2007), 906-913.
Yu, H., et al., "MinK-related peptide 1: A beta subunit for the HCN ion channel subunit family enhances expression and speeds activation", Circ. Res., 88(12), (Jun. 22, 2001), e84-7.
Zanon, F., et al., "A Feasible Approach for Direct His-Bundle Pacing Using a New Steerable Catheter to Facilitate Precise Lead Placement", Journal of Cardiovascular Electrophysiology, 17(1), (Jan. 2006), 29-33.
Zanon, Francesco, et al., "A New Technique for Direct His-Bundle Pacing: Acute and Mid-Term Electrical Data Results", [abstract] Oasis, (2006), 1 pg.
Zanon, Francesco, et al., "Direct His Bundle Pacing Preserves Coronary Perfusion Compared With Right Ventricular Apical Pacing: A Prospective, Cross-Over Mid-Term Study", Europace, vol. 10, (2008), 580-587.
Zhang, Y., et al., "His Electrogram Alternans Reveal Dual-Wavefront Inputs Into and Longitudinal Dissociation Within the Bundle of His", Circulation,104(7), (2001), 832-838.
Zhu, Q., et al., "Methods, Devices and Systems for Cardiac Pacing Therapies Using Intrinsic Activity", U.S. Appl. No. 61/139,117, filed Dec. 19, 2008, 22 pgs.
"U.S. Appl. No. 12/147,376, Notice of Allowance mailed Dec. 7, 2012", 7 pgs.
"U.S. Appl. No. 12/249,454, Notice of Allowance mailed Dec. 26, 2012", 5 pgs.
"U.S. Appl. No. 12/249,454, Response filed Dec. 4, 2012 to Non Final Office Action mailed Sep. 4, 2012", 12 pgs.
"U.S. Appl. No. 12/249,479, Notice of Allowance mailed Jan. 8, 2013", 5 pgs.
"U.S. Appl. No. 12/249,479, Response filed Dec. 4, 2012 to Non Final Office Action mailed Sep. 4, 2012", 9 pgs.
"U.S. Appl. No. 13/211,937, Non Final Office Action mailed Jan. 15, 2013", 7 pgs.
"U.S. Appl. No. 13/217,776, Non Final Office Action mailed Jan. 15, 2013", 6 pgs.
"European Application Serial No. 05849548.2, Office Action mailed Jan. 16, 2013", 3 pgs.
"International Application Serial No. PCT/US2011/033944, International Preliminary Report on Patentability mailed Nov. 8, 2012", 9 pgs.
"International Application Serial No. PCT/US2012/026571, International Search Report mailed Oct. 18, 2012", 4 pgs.
"International Application Serial No. PCT/US2012/026571, Written Opinion mailed Oct. 18, 2012", 7 pgs.
"Japanese Application Serial No. 2007-548289, Office Action mailed Nov. 6, 2012", With English Translation, 3 pgs.
"Japanese Application Serial No. 2007-548289, Response filed Feb. 4, 2013 to Office Action mailed Nov. 6, 2012", With English Claims, 7 pgs.
"Japanese Application Serial No. 2010-515189, Office Action mailed Feb. 12, 2013", With English Translation, 9 pgs.
"Japanese Application Serial No. 2010-515196, Office Action mailed Jan. 15, 2013", With English Translation, 8 pgs.
"Japanese Application Serial No. 2010-515198, Office Action mailed Feb. 12, 2013", With English Translation, 16 pgs.
"Japanese Application Serial No. 2011-531237, Office Action mailed Jan. 15, 2013", With English Translation, 7 pgs.
"Japanese Application Serial No. 2011-542513, Office Action mailed Jan. 15, 2013", With English translation, 6 pgs.
US 6,875,206, 04/2005, Ponzi (withdrawn)

\* cited by examiner

HIS-BUNDLE CAPTURE VERIFICATION AND MONITORING

CLAIM OF PRIORITY

This application claims the benefit of priority under 35 U.S.C. §119(e) of Dong et al., U.S. Provisional Patent Application Ser. No 61/328,248, entitled "HIS-BUNDLE CAPTURE VERIFICATION AND MONITORING", filed on Apr. 27, 2010, which is herein incorporated by reference in its entirety.

BACKGROUND

A medical device can be implanted in a body to perform one or more tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system.

In various examples, cardiac rhythm or function management devices can sense intrinsic heart contractions, deliver pacing pulses to evoke responsive heart contractions, or deliver a shock to interrupt certain arrhythmias. In certain examples, one or more of these functions can help improve a patient's heart rhythm or can help coordinate a spatial nature of a heart contraction, either of which can improve cardiac output of blood to help meet the patient's metabolic need for such cardiac output.

OVERVIEW

This document discusses, among other things, a system and method for generating a stimulation energy to provide His-bundle stimulation for a cardiac cycle, receiving electrical information from the heart over at least a portion of the cardiac cycle, determining a characteristic of at least a portion of the received electrical information for the cardiac cycle, and classifying the cardiac cycle using the determined characteristic.

In Example 1, a system includes a cardiac stimulation circuit configured to generate a stimulation energy to provide His-bundle stimulation for a cardiac cycle, a cardiac sensing circuit configured to receive electrical information from the heart over at least a portion of the cardiac cycle, and a processor configured to determine a characteristic of the received electrical information from the heart over at least a portion of the cardiac cycle using the received electrical information, wherein the processor is configured to classify the cardiac cycle using the determined characteristic.

In Example 2, the characteristic of the received electrical information of Example 1 optionally includes at least one of:
(1) a width of a QRS complex;
(2) an amplitude of the QRS complex;
(3) a slope of the QRS complex;
(4) a latency of the QRS complex;
(5) a correlation of the received electrical information to at least one of a myocardium capture template or a His-bundle capture template;
(6) a measure of a heart hemodynamic condition;
(7) a vector of the QRS complex; or
(8) a morphology of the QRS complex.

In Example 3, the processor of any one or more of Examples 1-2 is optionally configured to classify the cardiac cycle, using the determined characteristic, as at least one of:
(1) myocardium capture;
(2) His-bundle capture;
(3) partial His-bundle capture;
(4) AV node capture;
(5) non-capture; or
(6) fusion of at least one of myocardium capture, His-bundle capture, partial His-bundle capture, AV node capture, or non-capture.

In Example 4, the processor of one or more of Examples 1-3 is optionally configured to provide the classification to an external module, wherein the external module is configured to display a classification trend.

In Example 5, the processor of one or more of Examples 1-4 is optionally configured to classify a plurality of cardiac cycles, wherein the classification includes His-bundle capture, and wherein the classification trend includes a His-bundle capture trend.

In Example 6, the processor of one or more of Examples 1-5 is optionally configured to determine a His-bundle capture threshold using the determined characteristic.

In Example 7, the processor of one or more of Examples 1-6 is optionally configured to compare the determined characteristic with a corresponding characteristic from at least one of a myocardium capture template or a His-bundle capture template, and to determine a His-bundle capture threshold using the comparison.

In Example 8, the processor of one or more of Examples 1-7 is optionally configured to determine a first His-bundle capture threshold for a first pacing waveform and a second His-bundle capture threshold for a second pacing waveform, the second pacing waveform different than the first pacing waveform.

In Example 9, the processor of any one or more of Examples 1-8 is optionally configured to determine a first His-bundle capture threshold for a first pacing configuration and a second His-bundle capture threshold for a second pacing configuration, the second pacing configuration different than the first pacing configuration.

In Example 10, the processor of one or more of Examples 1-9 is optionally configured to recommend one of the first or second pacing configurations based on at least one of:
(1) a preferred pacing configuration;
(2) a pacing threshold; or
(3) a His-bundle capture quality.

In Example 11, a method includes generating a stimulation energy to provide His-bundle stimulation for a cardiac cycle, receiving electrical information from the heart over at least a portion of the cardiac cycle, determining a characteristic of at least a portion of the received electrical information for the cardiac cycle, and classifying the cardiac cycle using the determined characteristic.

In Example 12, the determining the characteristic of at least a portion of the received electrical information of one or more of Examples 1-11 includes determining at least one of:
(1) a width of an QRS complex;
(2) an amplitude of the QRS complex;
(3) a slope of the QRS complex;
(4) a latency of the QRS complex;
(5) a correlation of the received electrical information to at least one of a myocardium capture template or a His-bundle capture template;
(6) a measure of a heart hemodynamic condition;
(7) a vector of the QRS complex; or
(8) a morphology of the QRS complex.

In Example 13, the classifying the cardiac cycle of one or more of Examples 1-12 includes classifying the cardiac cycle as at least one of:
(1) myocardium capture;
(2) His-bundle capture;
(3) partial His-bundle capture;
(4) AV node capture;
(5) non-capture; or
(6) fusion of at least one of myocardium capture, His-bundle capture, partial His-bundle capture, AV node capture, or non-capture.

In Example 14, any one or more of Examples 1-13 optionally includes providing classification information to an external module, and displaying a classification trend.

In Example 15, the classifying the cardiac cycle of any one or more of Examples 1-14 optionally includes classifying a plurality of cardiac cycles into one or more class, wherein the class includes His-bundle capture, and wherein the classification trend includes a His-bundle capture trend.

In Example 16, any one or more of Examples 1-15 optionally includes determining a His-bundle capture threshold using the determined characteristic.

In Example 17, any one or more of Examples 1-16 optionally includes comparing the determined characteristic with a corresponding characteristic from at least one of a myocardium capture template or a His-bundle capture template, and determining a His-bundle capture threshold using the comparison.

In Example 18, any one or more of Examples 1-17 optionally includes determining a first His-bundle capture threshold for a first pacing waveform and a second His-bundle capture threshold for a second pacing waveform, the second pacing waveform different than the first pacing waveform.

In Example 19, any one or more of Examples 1-18 optionally includes determining a first His-bundle capture threshold for a first pacing configuration and a second His-bundle capture threshold for a second pacing configuration, the second pacing configuration different than the first pacing configuration.

In Example 20, any one or more of Examples 1-19 optionally includes recommending one of the first or second pacing configurations based on at least one of:
(1) a preferred pacing configuration;
(2) a pacing threshold; or
(3) a His-bundle capture quality.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The natural conduction pathway of the heart originates in the sinoatrial (SA) node in the right atrium of the heart. When functioning properly, the SA node is the primary natural pacemaker of the heart, generating intrinsic electrical impulses or action potentials, triggering the atria to contract. From the SA node, the conduction pathway follows internodal pathways to the atrioventricular (AV) node, located between the atrium and the ventricle. Following a delay at the AV node, conduction continues through the His-bundle to the left and right bundle branches, then to the purkinje fibers, to the apex of the heart, and finally up and around to the ventricular myocardium.

Cardiac contractions utilizing the natural conduction pathway, such as intrinsic contractions, are generally advantageous over typical apical or biventricular pacing, providing a faster, more focused and efficient contraction. Accordingly, providing stimulation energy (e.g., a pacing energy) to a portion of the natural conduction pathway (e.g., the His-bundle, etc.) can utilize the faster conducting fibers (in contrast to slower activating muscle cells), providing more physiological stimulation and better hemodynamic benefits.

Further, it is possible that the actual blockage in left bundle branch block (LBBB) can be located in the His-bundle. In these instances, cardiac resynchronization therapy with a single lead at the His-bundle (e.g., distal the blockage/defect) may be more effective than traditional biventricular pacing. However, His-bundle pacing, generally, has higher and unstable thresholds due to lead placement and difficulty in capturing the purkinje system.

Accordingly, the present inventors have recognized, among other things, a system and method for classifying a cardiac cycle (e.g., as partial or complete His-bundle capture, myocardium capture, AV-node capture, non-capture, etc.), for automatically determining a His-bundle threshold, for adjusting a pacing configuration, or for monitoring or reporting the stability of the His-bundle pacing.

Example Waveforms

Figure 1:
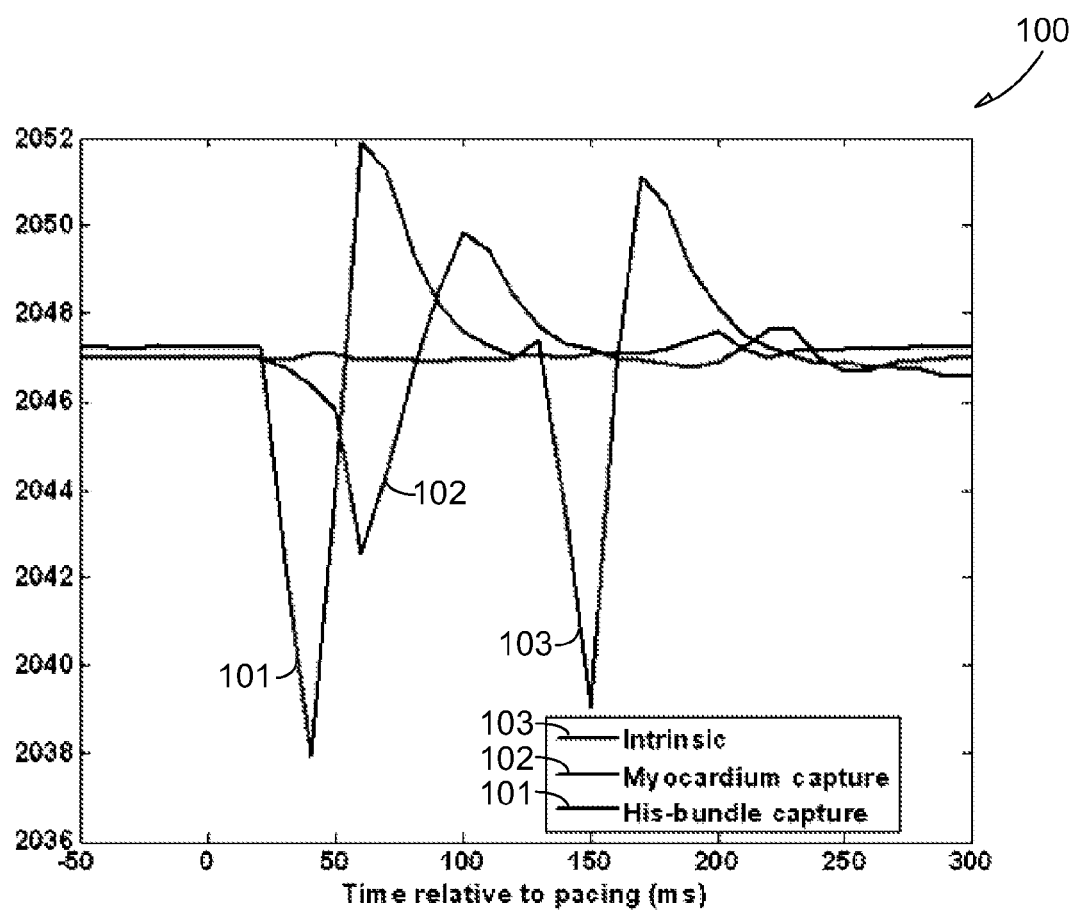
FIG. 1 illustrates generally an example of a relationship between different depolarizations.

FIG. 1 illustrates generally an example of a relationship 100 between three different depolarizations from an animal with normal intrinsic conduction, such as obtained using via an intracardiac electrogram (e.g., such as between a "can" electrode and an electrode of an implantable lead such as located within the right ventricle):
(1) a His-bundle capture 101;
(2) a myocardium capture 102; and
(3) an intrinsic depolarization 103.

As seen in the example of FIG. 1, the His-bundle capture 101 depolarization has a narrower width and higher slope than the myocardium capture 102, but a similar morphology to the intrinsic depolarization 103. The relationship 100 illustrates that the His-bundle capture 101 is advantageous to the myocardium capture 102 by utilizing the intrinsic electrical conduction pathways in the heart.

Example System Components

Figure 2:
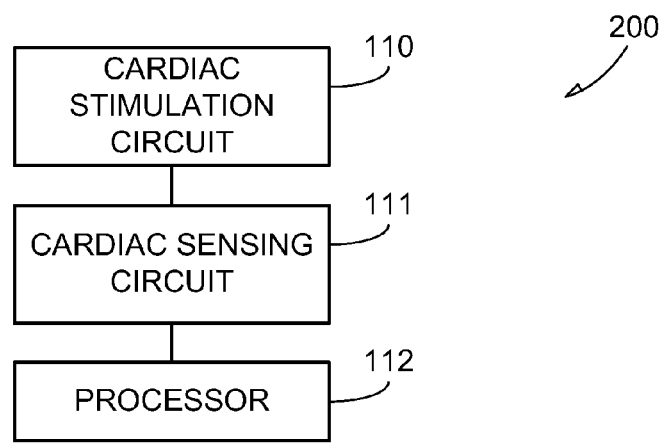
FIG. 2 illustrates generally an example of a system including a cardiac stimulating circuit, a cardiac sensing circuit, and a processor.

FIG. 2 illustrates generally an example of a system 200 including a cardiac stimulating circuit 110, a cardiac sensing circuit 111, and a processor 112. In an example, the cardiac stimulating circuit 110 can be configured to generate a stimulation energy configured to invoke a cardiac depolarization. In an example, the stimulation energy can be configured to provide His-bundle stimulation for a cardiac cycle. His-bundle stimulation can be provided, for example, from the right ventricle at one or more locations along the interventricular septum, the right ventricular outflow tract septum, or one or more other locations proximate the His-bundle.

In an example, the cardiac sensing circuit 111 can be configured to receive electrical information from the heart, for example, over at least a portion of the cardiac cycle the stimulation energy was generated for, above. In an example, the electrical information can include an electrical cardiogram (ECG) signal (e.g., an evoked response, a subcutaneous ECG, an intracardiac electrogram, or other), or one or more other electrical signals indicative of cardiac information (e.g., heart sounds, intrathoracic impedance, pressure, etc.). For example, such electrical information can be sensed using the cardiac sensing circuit 111 via one or more electrodes located within or near the heart (e.g., an implantable lead electrode or an electrode on the housing of the IMD), or located externally to the subject (e.g., such as a surface ECG).

The processor 112 can be configured to determine a characteristic of the received electrical information from the heart over at least a portion of the cardiac cycle using the received electrical information. For example, the characteristic of the received electrical information can correlate to the onset of a ventricular contraction (e.g., a Q wave, a QRS complex, or the like). In an example, the characteristics can include at least one of:

(1) a width of a QRS complex;
(2) an amplitude of the QRS complex;
(3) a slope of the QRS complex;
(4) a latency of the QRS complex;
(5) a correlation of the received electrical information to at least one of a myocardium capture template or a His-bundle capture template;
(6) a measure of a heart hemodynamic condition;
(7) a vector of the QRS complex; or
(8) a morphology of the QRS complex.

In an example, one or more other characteristics can be used, such as measures of contractility, synchrony, cardiac output, etc., a QRS axis/polarity or repolarization index (e.g., T-wave polarity, measures or surrogate measures of repolarization time, etc.), etc.

Further, in an example, the processor 112 can be configured to classify the cardiac cycle using the determined characteristic (e.g., using a detected change in the determined characteristic, comparing the determined characteristic to a threshold, etc.). In an example, the cardiac cycle can be classified as at least one of:

(1) myocardium capture;
(2) His-bundle capture;
(3) partial His-bundle capture;
(4) AV node capture;
(5) non-capture; or
(6) fusion of at least one of myocardium capture, His-bundle capture, partial His-bundle capture, or non-capture.

In other examples, one or more other classes can be used.

In an example, the processor 112 can be configured to report (or make available) one or more classifications or results from the classification to an external module (e.g., an external programmer, directly to a clinician's handheld mobile device, email, etc.). In an example, the processor 112 can be configured to classify a plurality of cardiac cycles, count or store one or more of the results from the classification, and, when the His-bundle capture percentage is below a threshold, the processor can be configured to do one or more of the following:

(1) provide an alert to an external module;
(2) reduce the stimulation energy to save power;
(3) increase the stimulation energy (e.g., the pacing threshold) to ensure His-bundle capture;
(4) switch to a different pacing configuration (e.g., different pacing waveform, site, etc.); or
(5) initiate a test to determine the His-bundle threshold.

In certain examples, the percentage of the His-bundle capture can be trended and the trending can be provided to an external module and displayed to the user.

In an example, the processor 112 can be configured to increase the stimulation energy (e.g., the pacing threshold) to increase the His-bundle capture percentage. In certain examples, the stimulation energy can be increased after a time interval (e.g., a number of hours, days, etc.), after a number of cardiac cycles, after a number of His-bundle captures, after a number of His-bundle non-captures, at a threshold His-bundle capture percentage, etc.

In an example, the processor 112 can be configured to determine a His-bundle capture threshold using one or more of the determined characteristics (e.g., QRS width, height, slope, etc.). For example, the His-bundle capture threshold can be used to create or update one or more of a myocardium capture template or a His-bundle capture template. In an example, the processor 112 can be configured to create or update one or more myocardium capture templates, or one or more His-bundle capture templates. Further, the processor 112 can be configured to compare the determined characteristic with a corresponding characteristic from at least one of a myocardium capture template or a His-bundle capture template, and to determine a His-bundle capture threshold or a myocardium capture threshold using the comparison. In certain examples, capture thresholds can be determined for a plurality of cardiac cycles, and a plurality of different pacing configurations, to determine an optimal suggested configuration. In certain examples, the optimum suggested configuration can be based on, among other things, a preferred pacing configuration, a pacing output or pacing output energy, a His-bundle capture quality (e.g., tallied over a plurality of cardiac cycles, including, for example, percentage of His-bundle captures, etc.).

Further, in certain examples, one or more templates (e.g., an individual template, or one or more of a group of templates) can be used to distinguish between partial and complete His-bundle capture. In certain examples, one or more defects in the natural conduction pathway (e.g., left or right bundle branch block, infarct, etc.) can inhibit a complete His-bundle capture, instead allowing only a partial His-bundle capture. In a partial His-bundle capture, a portion of the heart can utilize the faster conduction pathways of the purkinje fibers, etc., to quickly and efficiently depolarize, while another portion must rely on slower, less efficient cell-to-cell depolarization of the cardiac muscle, if any depolarization at all. In an example, one or more methods can be used to distinguish between complete and partial His-bundle capture, including:

(1) using multiple electrograms from different electrodes (e.g., to receive different local information regarding the shape and direction of the depolarization);

(2) using multi-channel subcutaneous or intracardiac ECG signals;

(3) using surface ECG axis changes (e.g., during device follow-up, or when surface ECG is available; or (4) using clinician triggered templates, or previously stored templates of different partial or complete His-bundle capture waveforms, etc.

Figure 6:
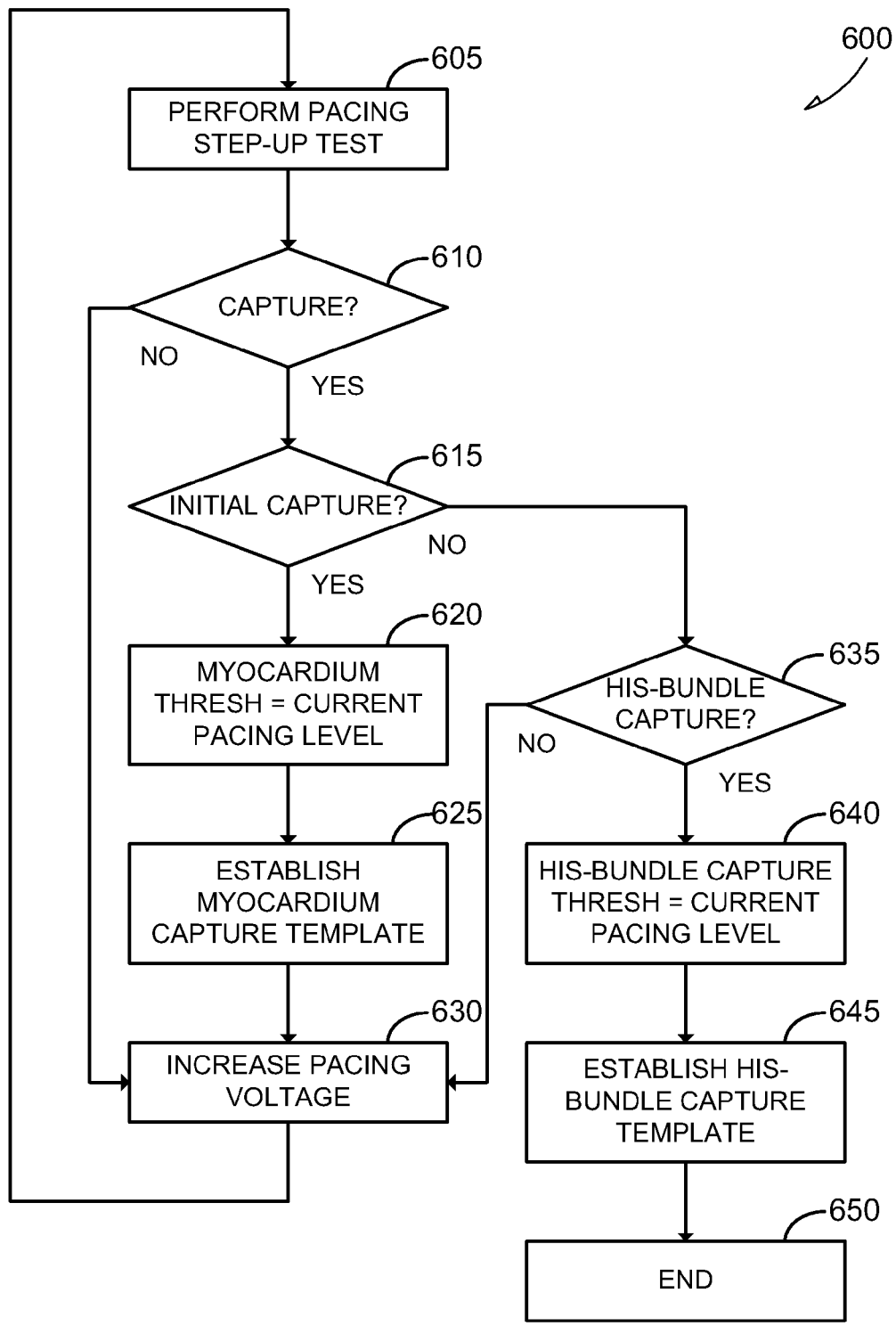
FIGS. 6-7 illustrate generally examples of methods of performing step-up or step-down tests to determine a His-bundle and a myocardium capture threshold.
Figure 7:
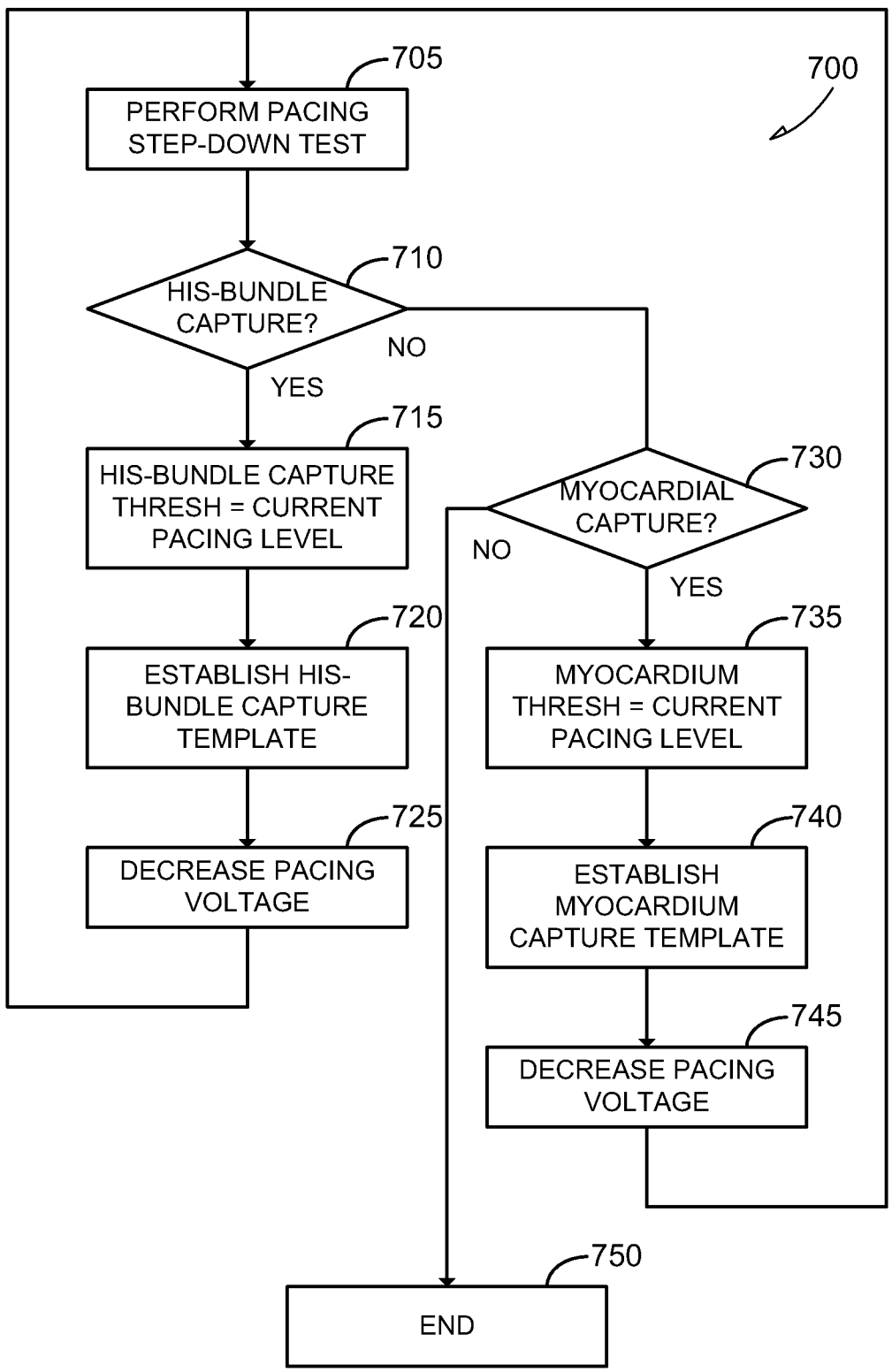

In an example, the clinician triggered templates, or previously stored templates can include an individually generated template (e.g., a template obtained from the subject 101 such as using the technique of FIG. 6 or 7, a template obtained from an individual of a population, etc.), or at least one of a group of templates corresponding to various degrees of His-bundle capture. For example, a group of templates can include templates indicative of at least one of His-bundle captured cardiac cycles, partial His-bundle captured cardiac cycles, myocardium captured cardiac cycles, non-captured cardiac cycles, etc. In an example, a template, or a group of templates, can be established using information obtained from a population. For example, one or more templates indicative of non-capture, partial His-bundle capture, myocardium capture, or complete His-bundle capture can be established from ECG information obtained from one or more subjects in a population.

Figure 3:
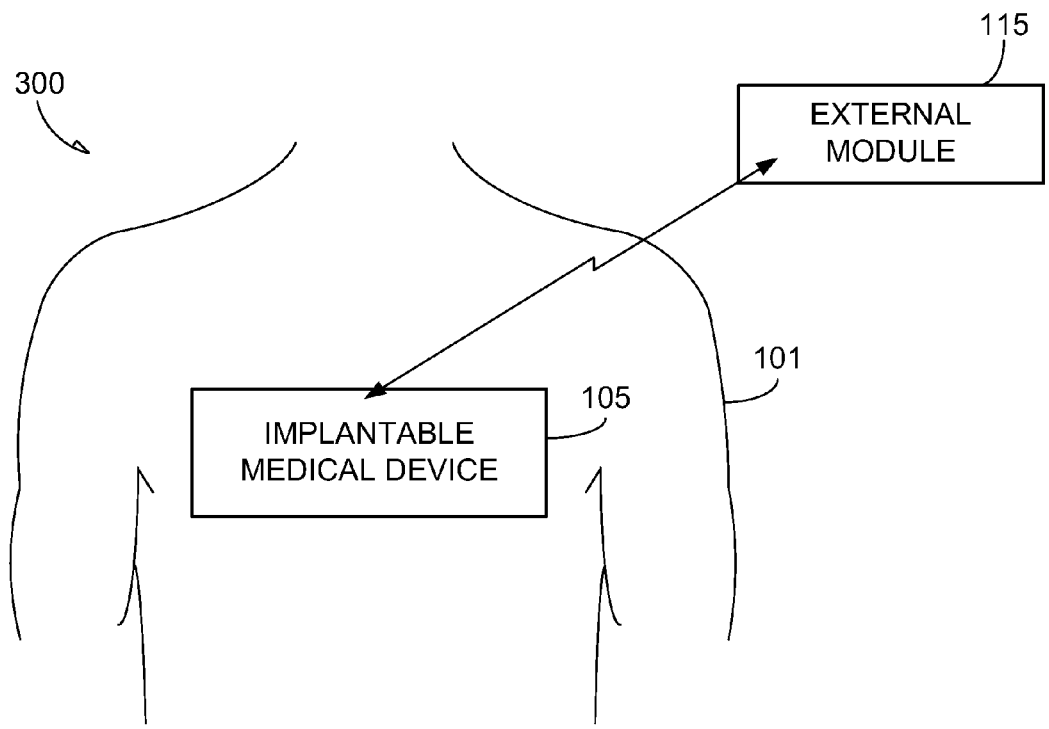
FIG. 3 illustrates generally an example of a system including an implantable medical device (IMD) in a subject, the IMD wirelessly coupled to an external module.

FIG. 3 illustrates generally an example of a system 300 including an implantable medical device (IMD) 105 in a subject 101, the IMD 105 wirelessly coupled to an external module 115. In an example, the IMD 105 can include one or more of the cardiac stimulation circuit 110, the cardiac sensing circuit 111, or the processor 112. In certain examples, a portion of the functionality of one or more of the cardiac stimulation circuit 110, the cardiac sensing circuit 111, or the processor 112 can occur in the IMD 105, and another portion elsewhere (e.g., in an external component, such as a 12-lead ECG, etc.).

In an example, the IMD 105 can include a pacemaker, a defibrillator, or one or more other implantable medical devices. In an example, the IMD 105 can include an antenna configured to provide radio-frequency or other communication between the IMD 105 and the external module 115 (or other external device).

In an example, the external module 115 can include an external antenna (e.g., or one or more external antennae). In an example, the external module 115 can include a local medical device programmer or other local external module (e.g., a medical device programmer or other external module within wireless communication of the IMD 105 antenna). In other examples, the external module 115 can include a remote medical device programmer or one or more other remote external modules (e.g., outside of wireless communication range of the IMD 105 antenna, but coupled to the IMD 105 using a local external device, such as a repeater). In an example, the external module 115 can be configured to send information to or receive information from the IMD 105. The information can include medical device programming information, subject data, device data, or other instructions, alerts, or other information. In an example, the external module 115 can be configured to display information (e.g., received information) to a user. Further, the local programmer or the remote programmer can be configured to communicate the sent or received information to a user or physician, such as by sending an alert via email of the status of the subject 101 or the system components.

Example Pacing Components

Figure 4:
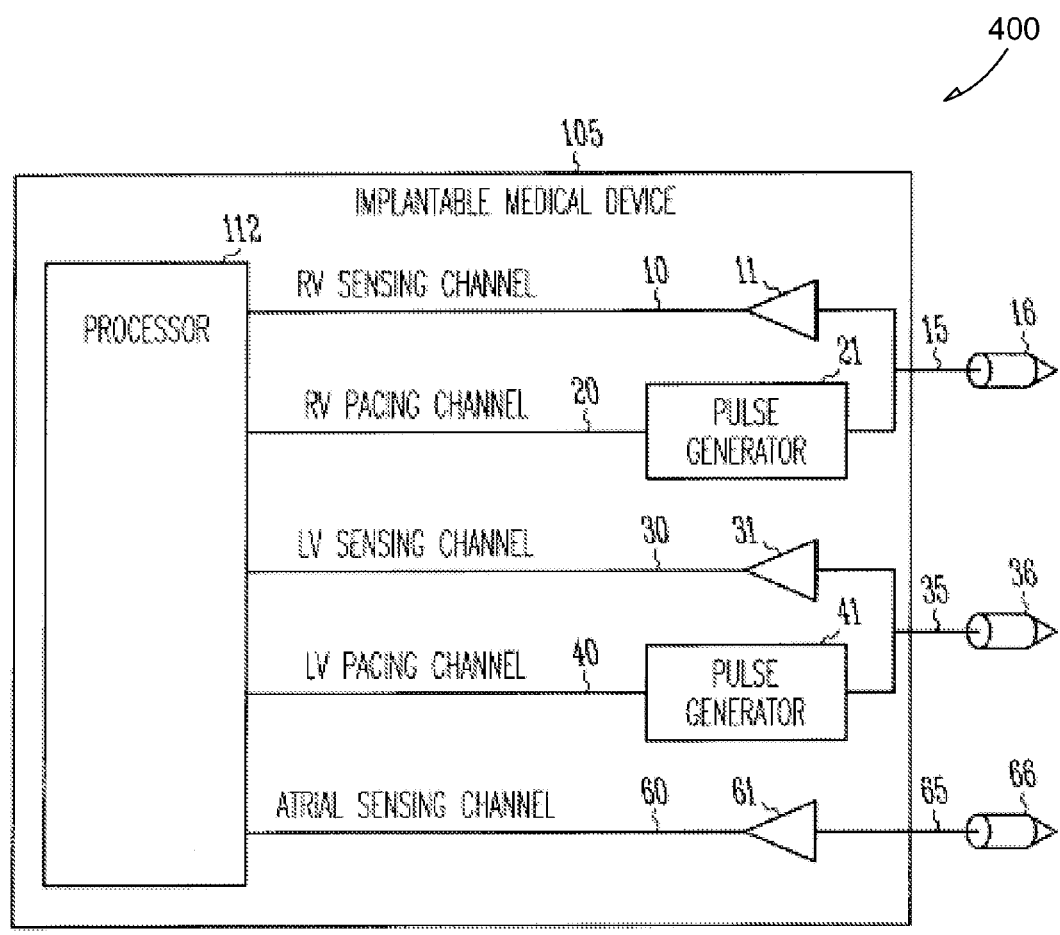
FIGS. 4-5 illustrate generally examples of systems or portions of a system for delivering cardiac therapy.

FIG. 4 illustrates generally an example of a system 400 for delivering stimulation energy to a subject. In an example, the system 400 can include an implantable medical device (IMD) 105 having a processor 112, a right ventricular sensing channel 10, a right ventricular pacing channel 20, a left ventricular sensing channel 30, a left ventricular pacing channel 40, and an atrial sensing channel 60.

The atrial sensing channel 60 can include at least one of a right atrial sensing channel or a left atrial sensing channel. In other examples, the IMD 105 can include a combination of at least one of the a right ventricular sensing channel 10, the right ventricular pacing channel 20, the left ventricular sensing channel 30, the left ventricular pacing channel 40, or the atrial sensing channel 60.

In certain examples, the right ventricular sensing channel 10 can include a sense amplifier 11, the left ventricular sensing channel 30 can include a sense amplifier 31, the right ventricle pacing channel 20 can include a pulse generator 21, the left ventricular pacing channel 40 can include a pulse generator 41, and the atrial sensing channel 60 can include a sense amplifier 61. In other examples, the right ventricular sensing channel 10 or the right ventricular pacing channel 20 can be coupled to an electrode 16 disposed on a lead 15 or elsewhere, the left ventricular sensing channel 30 or the left ventricular pacing channels 40 can be coupled to an electrode 36 disposed on a lead 35 or elsewhere, or the atrial sensing channel 60 can be coupled to an electrode 66 disposed on a lead 65 or elsewhere.

In certain examples, the lead 15 can be configured to electrically couple the sense amplifier 11 or the pulse generator 21 to the electrode 16, which can be configured to be located in a right ventricle, such as in the septal region, the right ventricular outflow tract, the free wall region, or another region of the right ventricle. Similarly, the lead 35 can be configured to electrically couple the sense amplifier 31 or the pulse generator 41 to the electrode 36, which can be configured to be located in, on, or near a left ventricle, such as in the septal region, the free wall region, or another region of the left ventricle or in the coronary vasculature. Further, the lead 65 can be configured to electrically couple the sense amplifier 61 to the electrode 66, which can be configured to be located in at least one of a right atrium or a left atrium of the subject 101.

In certain examples, the IMD 105 can include one or more other pacing or sensing channels, such as an atrial pacing channel, an internal thoracic pacing or sensing channel configured to couple the processor 112 to an internal thoracic location external to the heart (e.g., through one or more leads, electrodes, pulse generators, or sense amplifiers), one or more other atrial or ventricular pacing or sensing channels, etc. In an example, the internal thoracic pacing or sensing channel can be configured to send or receive information to or from a housing "can" electrode, located on the exterior housing of an implantable medical device located in the internal thoracic location external to the heart. In other examples, the IMD 105 can include one or more other right or left ventricular sensing or pacing channels, such as a right ventricular apex backup pacing channel, should His-bundle pacing become unreliable or the threshold increase beyond a safe level.

In the example of FIG. 4, the processor 112 can be an implantable component, an external component, or a combination or permutation of an implantable processor and an external processor. In an example, if at least a portion of the processor 112 includes an external processor, then the processor 112 can be configured to be communicatively coupled (such as via telemetry, RF, or other communication protocol)

with the remaining implantable components (such as the sense amplifier 11, 31, the pulse generator 21, 41, the lead 15, 35, or the electrode 16, 36). In an example, the implantable processor can be configured to have reduced or minimal functionality or power consumption. In certain examples, it can be advantageous for the processor 112 to include an external processor for computing complex operations or to store large amounts of information. In other examples, the external processor can include an external device that can be either local or remote. In an example, the processor 112 can include a microcontroller, a microprocessor, a logic circuit, or other processor.

Similar to the example illustrated in FIG. 2, the cardiac stimulation circuit 110 can include the pulse generator 11, and the cardiac sensing circuit 111 can include the pulse generator 21.

Figure 5:
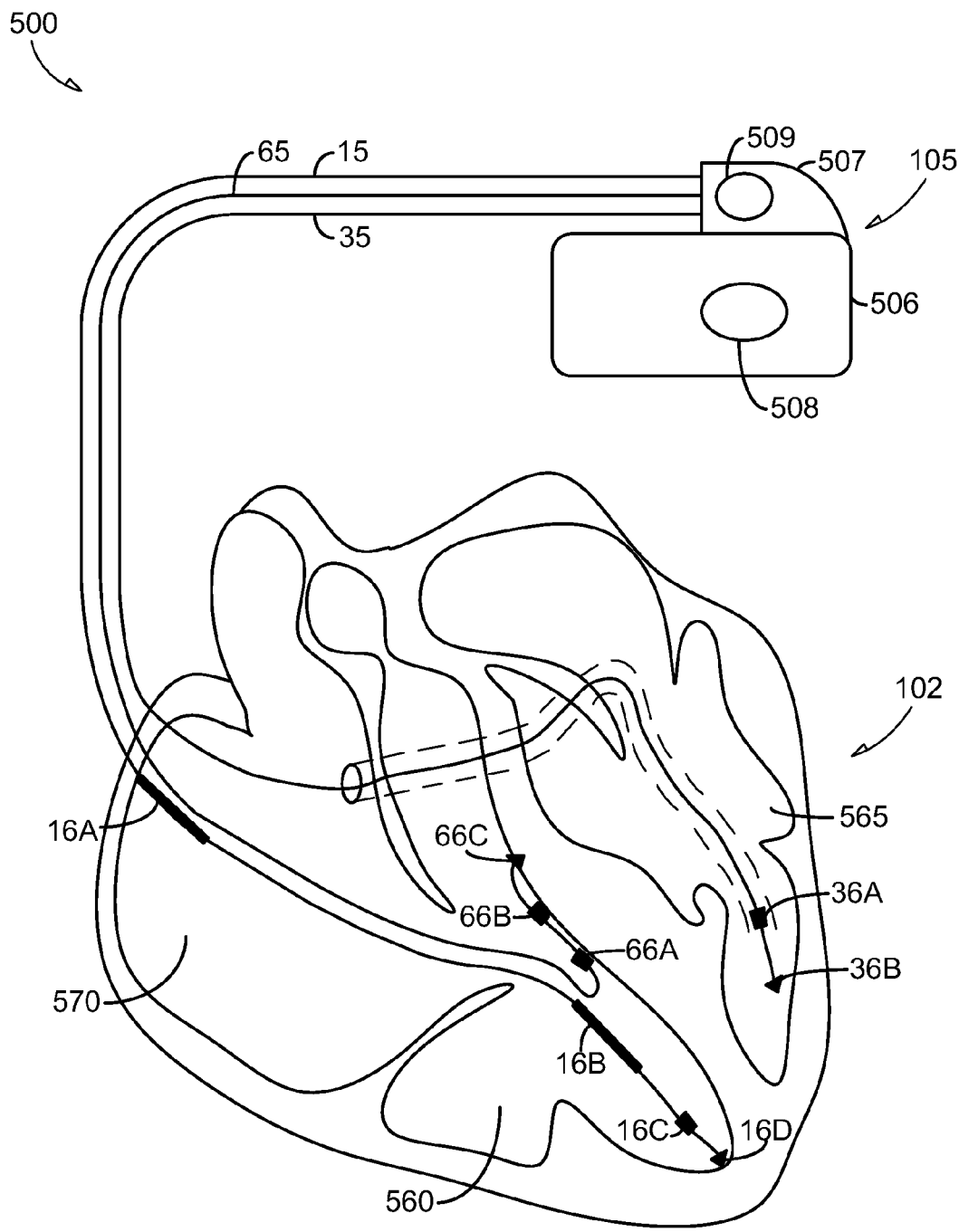

FIG. 5 illustrates generally an example of a system 500 including an IMD 105, a right ventricular apex lead 15, a left ventricular lead 35, a right ventricular septum lead 65. The IMD 105 can include a housing 506 (or CAN) and a header 507. In an example, at least a portion of the exterior of the housing 506 or the header 507 can include an electrode, herein referred to as the housing can electrode 508, or a header electrode 509.

The right ventricular apex lead 15 can include a first electrode 16A configured to be located in the superior vena cava of a heart 102, and a second electrode 16B, a third electrode 16B, and a fourth electrode 16D configured to be located in the right ventricle 560 of the heart 102. In an example, one or more electrodes, such as the first electrode 16A or the second electrode 16B, can include a shocking coil electrode configured to deliver a high energy shock (e.g., 0.1 Joule or greater, etc.) to the heart. In certain examples, the first electrode 16A can include a proximal defibrillation coil electrode and the second electrode 16B can include a distal defibrillation coil electrode.

The left ventricular lead 35 can include a fifth electrode 36A and a sixth electrode 36B configured to be located in, on, or near the left ventricle 565 of the heart 102, such as within the coronary vasculature. In an example, the sixth electrode 36B can include a distal pacing or sensing electrode. The right ventricular septum lead 65 can include a seventh electrode 66A, an eighth electrode 66B, and a ninth electrode 66C configured to be located along the septum in the right ventricle 560 of the heart 102. In an example, the right ventricular septum lead 65 can be configured to provide His-bundle pacing along the septum wall. In certain examples, the housing can electrode 508 can be electrically coupled to at least one other electrode (e.g., the first electrode 16A), or the housing can electrode 508 can be electrically isolated from other electrodes and capable of independent control. Further, in certain examples, the first electrode 16A through the ninth electrode 66C can include at least one of a coil-type electrode, a ring-type electrode, or a tip electrode.

In certain examples, the right ventricular apex lead 15 can be configured to electrically couple the IMD 105 to at least one of the right ventricle 560, the right atrium 570, or the superior vena cava using at least one electrode (e.g., the first electrode 16A, the second electrode 16B, the third electrode 16C, or the fourth electrode 16D), the left ventricular lead 35 can be configured to electrically couple the IMD 105 to the left ventricle 565 using at least one electrode (e.g., the fifth electrode 36A or the sixth electrode 36B), or the right ventricular septum lead 65 can be configured to electrically couple the IMD 105 to the interventricular septum using at least one electrode (e.g., the seventh electrode 66A, the eighth electrode 66B, or the ninth electrode 66C). In an example, at least one of the second electrode 16B, the third electrode 16C, or the fourth electrode 16D, can be configured to be located in, on, or near a right apical region of the heart 102. In other examples, the fifth electrode 36A or the sixth electrode 36B can be configured to be located in, on, or near a left apical region of the heart 102 or a left ventricular free lateral wall of the heart 102.

In certain examples, a cardiac rhythm management device capable of delivering a defibrillation energy can include a shocking electrode, such as the first electrode 16A, electrically tied or coupled to the housing can electrode.

Step-Up/Step-Down Examples

FIGS. 6-7 illustrate generally examples of methods 600, 700 of performing step-up or step-down tests to determine a His-bundle and a myocardium capture threshold. In certain examples, the pacing step-up or step-down tests can be performed after a number of cardiac cycles, after a time period, after a predefined condition is met (e.g., a number of failed His-bundle captures, etc.), or after one or more other conditions are met. In other examples, other tests can be performed to automatically determine a His-bundle capture threshold. In an example, a processor, such as the processor 112 of FIG. 2, can be configured to automatically determine one or more of a myocardium capture template, a His-bundle capture template, or a partial His-bundle capture template such as by using the step-up test or the step-down test, as described in FIGS. 6-7. In an example, step-up test information or step-down test information (e.g., the His-bundle capture threshold, the myocardium capture threshold, the stimulation energy level, or cardiac electrical information in response to the stimulation energy) can be presented to a user, such as by using the . The user can use the step-up test information or step-down test information to determine or supplement at least a portion of one or more of the myocardium capture template, the His-bundle capture template, or the partial His-bundle capture template.

FIG. 6 illustrates generally an example of a method 600 including determining a His-bundle capture threshold using a step-up test. At 605, a pacing step-up test is performed, including delivering a stimulation energy (e.g., a pacing voltage). In an example, the pacing step-up test can begin at a level previously known to not cause capture, or not likely to cause capture.

At 610, if no capture is detected, then, at 630, the pacing voltage is increased. In an example, a non-capture template can be established. Then, at each subsequent step-up test, the previous non-capture template can be supplemented, or replaced. At 605, the pacing step-up test is performed, including delivering the stimulation energy.

At 610, if capture is detected, and. at 615, initial capture is determined, then, at 620, the current pacing level is set as the myocardium capture threshold. At 625, a myocardium capture template is established.

In an example, the myocardium capture template can be established using the first initial capture. Then, at each subsequent step-up test, the previous myocardium capture template can be supplemented, or replaced. Various statistical techniques can be used to supplement a previous template (e.g., a moving average, etc.). In other examples, a clinical myocardium capture template can be used initially and supplemented or replaced. One or more of a group of myocardium capture templates can be used to determine myocardium capture or His-bundle capture (e.g., comparing one or more characteristics, correlating the current waveform to the template, etc.).

At 630, the pacing voltage is increased, and, at 605, the pacing step-up test is performed again, including delivering the stimulation energy.

At 615, if the detected capture is not the first capture since the initial pacing step-up test during this session, then, at 635, His-bundle capture is determined. At 635, several criteria can be investigated to determine if the detected capture is His-bundle capture. For example, the electrical information (e.g., a QRS waveform, etc.) from the heart can be correlated with an intrinsic capture, such as the subject's previously captured intrinsic waveform or a clinical intrinsic waveform. In other examples, the electrical information can be compared with the myocardium capture template, a physician triggered template, or a His-bundle capture template. In an example, His-bundle capture can be determined using one or more characteristics of the electrical information, such as:

(1) QRS width (e.g., a reduction of QRS width from myocardium capture, an increase pacing voltage coupled with a reduction of QRS width, comparison of intrinsic QRS width, etc.);

(2) QRS amplitude (e.g., a change in QRS amplitude, such as an increase in QRS amplitude over myocardium capture, comparison of intrinsic QRS amplitude, etc.);

(3) dV/dt (e.g., an increase in the slope of the QRS complex);

(4) QRS latency;

(5) Correlation to myocardium capture template;

(6) Normalization of the QRS axis vector; or (7) Indication of synchronization using other hemodynamic sensors (e.g., heart sounds, blood pressure, respiration, etc.).

At 635, if His-bundle capture (e.g., partial His-bundle capture, or complete His-bundle capture) is not detected, then, at 630, the pacing voltage is increased, and, at 605, the pacing step-up test is performed again, including delivering the stimulation energy. At 635, if His-bundle capture is detected, then, at 640, the current pacing level is set as the His-bundle capture threshold.

At 645, one or more of a group of His-bundle capture templates can be established, such as to correlate to a degree of His-bundle capture (e.g., partial His-bundle capture, complete His-bundle capture, myocardium capture, non-capture etc.). In an example, the His-bundle capture template can be established using the first initial His-bundle capture. Then, at each subsequent step-up test, the previous His-bundle capture template can be supplemented, or replaced. In an example, the myocardium capture template, the non-capture template, the His-bundle capture templates established during the first initial His-bundle capture, or one or more of the subsequent step-up tests can be included in a group of His-bundle capture templates. The group of His-bundle capture templates can include two or more templates corresponding to various degrees of capture (e.g., non capture, one or more degrees of partial His-bundle capture, complete His-bundle capture, myocardium capture, AV-node capture, etc.). Various statistical techniques can be used to supplement a previous template (e.g., a moving average, etc.). In other examples, a clinical His-bundle capture template can be used initially and supplemented or replaced. The His-bundle capture templates can be used to determine His-bundle capture or myocardium capture (e.g., comparing one or more characteristics, correlating the current waveform to the template, etc.). At 650, the pacing step-up test is ended.

In certain examples, during the step-up test, pacing may directly capture the His-bundle without first capturing the myocardium. In this case, when it is determined that the pace has captured the heart, the His-bundle capture criteria will be directly evaluated no matter whether it is the initial capture or not.

FIG. 7 illustrates generally an example of a method 700 including determining a His-bundle capture threshold using a step-down test. At 705, a pacing step-down test is performed, including delivering stimulation energy (e.g., a pacing voltage). In an example, the pacing step-down test can begin at or above a level previously known to cause capture, or likely to cause capture.

At 710, if His-bundle capture is detected, then, at 715, the current pacing level is set as the His-bundle capture threshold. At 720, a His-bundle capture template is established. At 725, the pacing voltage is decreased, and, at 705, the step-down pacing test is performed.

At 710, if His-bundle capture is not detected, and, at 730, myocardium capture is detected, then, at 735, the current pacing level is set as the myocardium threshold. At 740, a myocardium capture template is established. At 745, the pacing voltage is decreased and at 705, the step-down pacing test is performed. At 730, if no myocardium capture is detected, then, at 750, the step-down pacing test is ended.

In other examples, a step-up threshold test can be performed. At each increase in pacing voltage, a determined characteristic can be compared to a corresponding characteristic or characteristic template. In an example, the capture (e.g., the His-bundle capture, the myocardium capture, etc.) can be detected, or the threshold (e.g., the His-bundle capture threshold, the myocardium capture threshold, etc.) can be determined, if the determined characteristic matches the corresponding characteristic (e.g., autocorrelation coefficient reaches a maximum, etc.).

Reporting Example

Figure 8:
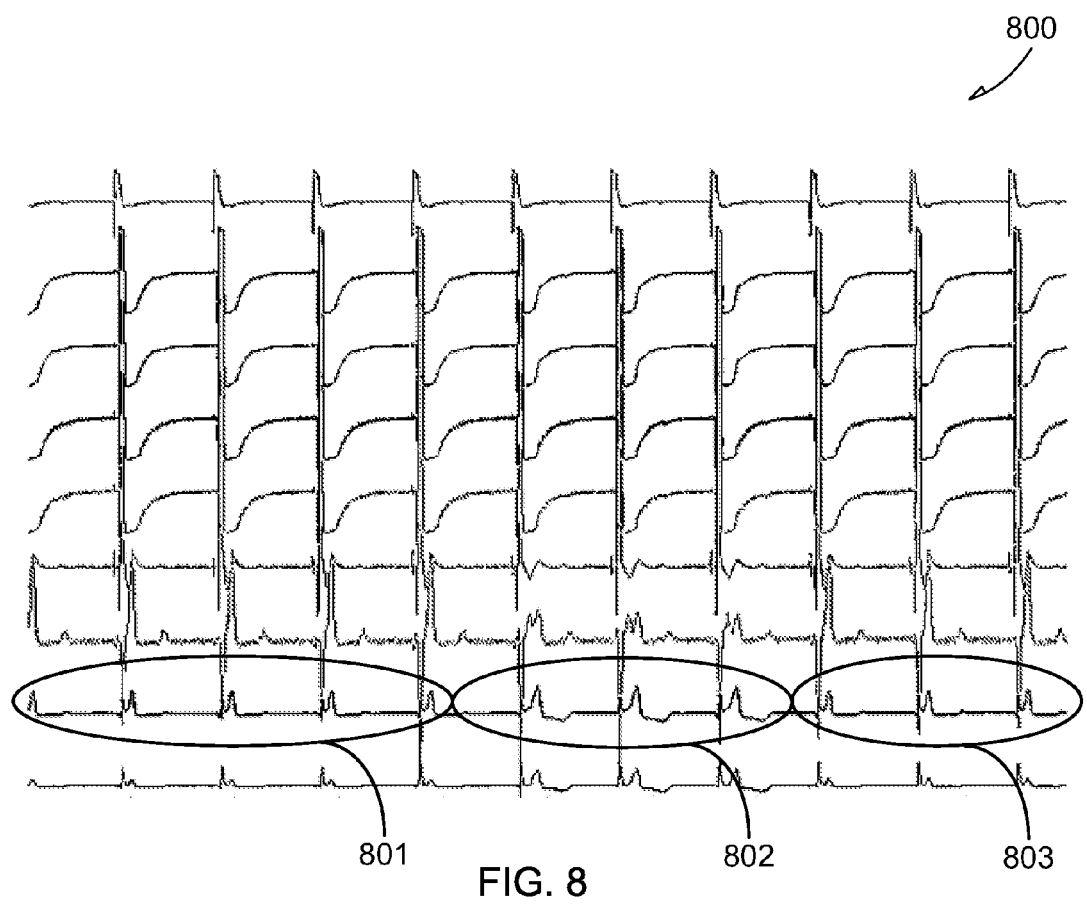
FIG. 8 illustrates generally an example of a relationship including His-bundle pacing intermittency on a set of ECG waveforms.

FIG. 8 illustrates generally an example of a relationship 800 including His-bundle pacing intermittency on a set of ECG waveforms. The relationship 800 includes a first set of His-bundle captured cardiac cycles 801, a first set of myocardium captured cardiac cycles 802, followed by a second set of His-bundle captured cardiac cycles 803.

In an example, the system or method disclosed herein can report His-bundle captured cardiac cycles, partial His-bundle captured cardiac cycles, myocardium captured cardiac cycles, non-captured cardiac cycles, etc. In an example, each cardiac cycle can be classified. If His-bundle capture falls below a percentage, a new His-bundle threshold test can be triggered and a pacing parameter can be adjusted. If a His-bundle capture percentage is below a threshold an alert can be issued to physicians and pacing output can be reduced to save energy. Further, in certain examples, this or other information can be trended and displayed (e.g., using the external module).

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   a cardiac stimulation circuit configured to generate a stimulation energy to provide His-bundle stimulation for multiple cardiac cycles;
   a cardiac sensing circuit configured to receive electrical information from the heart over at least a portion of the multiple cardiac cycles;
   a processor configured to determine characteristics of the received electrical information from the heart over the at least a portion of the multiple cardiac cycles using the received electrical information, the characteristics corresponding to individual ones of the multiple cardiac cycles;
   wherein the processor is configured to classify each cardiac cycle of the multiple cardiac cycles as a capture type using the respective determined characteristics, wherein the classifying includes distinguishing, for each cardiac cycle, a His-bundle capture type from (1) a myocardium-cell-to-myocardium-cell capture type, (2) an AV node capture type, and (3) a fusion capture type, the fusion capture type including at least partial intrinsic cardiac function fused with at least one of partial His-bundle capture, myocardium-cell-to-myocardium-cell capture, and AV node capture; and
   wherein the processor is configured to identify a His-bundle capture percentage using information about the classified cardiac cycles.

2. The system of claim 1, wherein at least one of the characteristics of the received electrical information includes at least one of:
   (1) a correlation of the received electrical information to at least one of a myocardium capture template or a His-bundle capture template;
   (2) a measure of a heart hemodynamic condition;
   (3) a vector of a QRS complex; or
   (4) a morphology of the QRS complex.

3. The system of claim 1, wherein the classifying includes distinguishing, for each cardiac cycle, the His-bundle capture type from two or more of:
   (1) a myocardium-cell-to-myocardium-cell capture type,
   (2) an AV node capture type, and
   (3) a fusion capture type, the fusion capture type including at least partial intrinsic cardiac function fused with at least one of partial His-bundle capture, myocardium-cell-to-myocardium-cell capture, and AV node capture.

4. The system of claim 1, wherein the processor is configured to provide the classification of the multiple cardiac cycles to an external module; and
   wherein the external module is configured to display a classification trend using the information about the classified cardiac cycle.

5. The system of claim 1, wherein the processor is configured to determine a complete or partial His-bundle capture threshold using the determined characteristic.

6. The system of claim 5, wherein the processor is configured to include a His-bundle capture template and to compare the determined characteristics with corresponding characteristics from the His-bundle capture template, and to determine a His-bundle capture threshold using the comparison.

7. The system of claim 5, wherein the processor is configured to determine a first His-bundle capture threshold for a first pacing waveform and a second His-bundle capture threshold for a different second pacing waveform.

8. The system of claim 5, wherein the processor is configured to determine a first His-bundle capture threshold for a first pacing configuration and a second His-bundle capture threshold for a different second pacing configuration.

9. The system of claim 8, wherein the processor is configured to include at least one of:
   (1) a preferred pacing configuration;
   (2) a pacing threshold; or
   (3) a His-bundle capture quality; and
   wherein the processor is configured to recommend one of the first or second pacing configurations based on the at least one of:
   (1) the preferred pacing configuration;
   (2) the pacing threshold; or
   (3) the His-bundle capture quality.

10. The system of claim 5, wherein the processor is configured to include one or more characteristic from a myocardium capture template that correspond to the determined characteristics, and wherein the processor is configured to compare the determined characteristics with corresponding characteristics from the myocardium capture template, and to determine a His-bundle capture threshold using the comparison.

11. The system of claim 5, wherein the processor is configured to include one or more characteristics from a His-bundle capture template that correspond to the determined characteristics, and wherein the processor is configured to compare the determined characteristics with corresponding characteristics from the His-bundle capture template, and to determine a myocardium capture threshold using the comparison.

12. The system of claim 5, wherein the processor is configured to include one or more characteristics from a myocardium capture template that correspond to the determined characteristics, and wherein the processor is configured to compare the determined characteristics with corresponding characteristics from the myocardium capture template, and to determine a myocardium capture threshold using the comparison.

13. The system of claim 7, wherein the processor is configured to include at least one of a pacing threshold or a His-bundle capture quality, and wherein the processor is configured to recommend one of the first or second waveforms based on the at least one of the pacing threshold or the His-bundle capture quality.

14. The system of claim 1, wherein at least one of the characteristics of the received electrical information includes at least one of a width or an amplitude of a QRS complex.

15. The system of claim 1, wherein at least one of the characteristics of the received electrical information includes at least one of a slope or a latency of a QRS complex.

16. The system of claim 1, wherein at least one of the characteristics of the received electrical information includes at least one of:
(1) a contractility measure;
(2) a synchrony measure;
(3) a cardiac output; or
(4) an indication of a repolarization time.

17. A system comprising:
a cardiac stimulation circuit configured to generate a stimulation energy to provide His-bundle stimulation for multiple cardiac cycles;
a cardiac sensing circuit configured to receive electrical information from the heart over at least a portion of the multiple cardiac cycles; and
a processor configured to determine characteristics of the received electrical information from the heart over the at least a portion of the multiple cardiac cycles using the received electrical information, the characteristics corresponding to individual ones of the multiple cardiac cycles;
wherein the processor is configured to determine a His-bundle capture threshold using the determined characteristics;
wherein the processor is configured to classify each cardiac cycle of the multiple cardiac cycles as a capture type using the respective determined characteristics, wherein the classifying includes distinguishing, for each cardiac cycle, a complete His-bundle capture type from a partial His-bundle capture type, and wherein the processor is configured to determine a His-bundle capture percentage, using information about the classified cardiac cycles; and
when the His-bundle capture percentage is less than a threshold percentage, the processor is configured to determine a different His-bundle capture threshold.

18. A system comprising:
a cardiac stimulation circuit configured to generate a stimulation energy to provide His-bundle stimulation for multiple cardiac cycles;
a cardiac sensing circuit configured to receive electrical information from the heart over at least a portion of the multiple cardiac cycles; and
a processor configured to determine characteristics of the received electrical information from the heart over the at least a portion of the multiple cardiac cycles using the received electrical information, the characteristics corresponding to individual ones of the multiple cardiac cycles, wherein the characteristics of the received electrical information include characteristics of QRS complexes associated with respective ones of the multiple cardiac cycles;
wherein the processor is configured to classify each cardiac cycle of the multiple cardiac cycles, using the respective determined characteristics, wherein the classifying includes distinguishing, for each cardiac cycle, a complete His-bundle capture type from a partial His-bundle capture type.

* * * * *